(12) United States Patent
Fukuzawa et al.

(10) Patent No.: US 9,186,099 B2
(45) Date of Patent: Nov. 17, 2015

(54) LANCET CARTRIDGE

(71) Applicant: ARKRAY, INC., Kyoto (JP)

(72) Inventors: Masahiro Fukuzawa, Kyoto (JP);
Susumu Nishino, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 179 days.

(21) Appl. No.: 13/708,443

(22) Filed: Dec. 7, 2012

(65) Prior Publication Data

US 2013/0165961 A1  Jun. 27, 2013

(30) Foreign Application Priority Data

Dec. 9, 2011 (JP) ................................. 2011-270037

(51) Int. Cl.
*A61B 5/15* (2006.01)
*A61B 5/151* (2006.01)

(52) U.S. Cl.
CPC .......... *A61B 5/1411* (2013.01); *A61B 5/150022* (2013.01); *A61B 5/15113* (2013.01); *A61B 5/15117* (2013.01); *A61B 5/15128* (2013.01); *A61B 5/15142* (2013.01); *A61B 5/150175* (2013.01); *A61B 5/150305* (2013.01); *A61B 5/150435* (2013.01); *A61B 5/150519* (2013.01); *A61B 5/150564* (2013.01); *A61B 5/150618* (2013.01); *A61B 5/150717* (2013.01); *A61B 5/150824* (2013.01); *A61B 5/150893* (2013.01); *A61B 5/150259* (2013.01)

(58) Field of Classification Search
CPC ........... A61B 5/1411; A61B 5/150022; A61B 5/15186; A61B 5/15117; A61B 5/14532; A61B 5/150412; A61B 5/15113; A61B 5/15146; A61B 5/15142; A61B 5/1519; A61B 5/150717; A61B 5/1513; A61B 5/150519; A61B 5/150618; A61B 5/151; A61B 5/150549; A61B 5/15194; A61B 5/150282; A61B 17/32093
USPC ........... 606/181–183, 167; 600/581–583, 573
See application file for complete search history.

(56) References Cited

U.S. PATENT DOCUMENTS

| | | | |
|---|---|---|---|
| 5,964,718 A | 10/1999 | Duchon et al. | |
| 6,053,930 A * | 4/2000 | Ruppert | 606/181 |
| 6,066,103 A | 5/2000 | Duchon et al. | |
| 6,464,649 B1 | 10/2002 | Duchon et al. | |
| 6,969,359 B2 | 11/2005 | Duchon et al. | |
| 7,481,818 B2 * | 1/2009 | Allen et al. | 606/181 |
| 2003/0018300 A1 | 1/2003 | Duchon et al. | |
| 2004/0127818 A1 * | 7/2004 | Roe et al. | 600/583 |
| 2004/0260326 A1 | 12/2004 | Lipoma et al. | |
| 2006/0058827 A1 * | 3/2006 | Sakata | 606/181 |
| 2008/0082023 A1 * | 4/2008 | Deck et al. | 600/583 |
| 2009/0143810 A1 * | 6/2009 | Kitamura et al. | 606/182 |

FOREIGN PATENT DOCUMENTS

| | | |
|---|---|---|
| DE | 298 09 758 U1 | 8/1998 |
| EP | 1 897 493 A1 | 3/2008 |
| JP | 2004-237089 A | 8/2004 |

(Continued)

*Primary Examiner* — Jocelin Tanner

(74) *Attorney, Agent, or Firm* — Studebaker & Brackett PC

(57) ABSTRACT

A lancet cartridge is provided with a skin contact section that is held in the interior of a lancet holder and that includes a second pricking opening. A first pricking opening is formed to a size such that a skin contact section can be accommodated therein. Upon pressing in the pricking direction, the skin contact section is accommodated in the first pricking opening, and the leading end section of a pricking member protrudes through the second pricking opening.

15 Claims, 15 Drawing Sheets

(56) References Cited

FOREIGN PATENT DOCUMENTS

| | | |
|---|---|---|
| JP | 2005-046612 A | 2/2005 |
| JP | 2012-020164 A | 2/2012 |
| WO | 03/022331 A2 | 3/2003 |
| WO | 2009/041110 A1 | 4/2009 |
| WO | 2009/145920 A1 | 12/2009 |

* cited by examiner

LANCET CARTRIDGE

BACKGROUND OF THE INVENTION

1. Field of the Invention

The present invention relates to a lancet cartridge that is used during collection of body fluids for use in a handy measuring instrument or the like.

2. Description of the Related Art

Compact measuring instruments are used for measuring the amount of components, for instance, glucose or cholesterol, in body fluids. A small amount of body fluid is necessary for measurement using these handy measuring instruments. For instance, in order to collect a small amount of a body fluid, a pricking instrument is used wherein a disposable lancet is fitted to a main body having a lancet-ejecting mechanism, after which an end cap is fitted to the leading end of the main body. A pricking opening is provided in the leading end of the end cap. The leading end of the end cap is pressed against the skin of the test subject, and the main body is operated; thereby, the leading end section of the lancet is caused to protrude through the pricking opening, and to prick the skin of the test subject, to collect the body fluid as a result. The following conventional approaches are adopted in order to secure a body fluid amount that is sufficient for measurement, upon collection of a body fluid using such a pricking instrument.

For instance, Japanese Patent Application Publication No. 2005-046612 discloses the feature of preparing multiple end caps having dissimilar sizes, in order to modify the depth of the leading end section of the lancet that penetrates the skin. Japanese Patent Application Publication No. 2004-237089 discloses the feature of preparing a plurality of end caps having leading end shapes that conform to the shape of collection sites, to enable appropriate collection of a body fluid at a plurality of dissimilar collection sites, for instance the fingertip, the forearm and the like.

If blood sampling is performed using a pricking instrument that is shared among a plurality of test subjects, problems of hygiene arise in that body fluids become adhered to the leading end of the end cap, and in that the leading end section of the pricking member, with the body fluid adhered thereto, becomes exposed. In order to solve the above problems, for instance, WO 2009/041110 discloses a lancet cartridge in which a lancet is integrally housed in a lancet holder. The lancet holder, having a pricking opening formed at the leading end, has the same function as the aforementioned end cap, but is disposed of together with the lancet, even if a body fluid is adhered to the leading end. Also, the lancet is housed in the lancet holder, except during pricking. Therefore, the leading end section of the lancet having a body fluid adhered thereto does not come into contact with an operator or the like. Therefore, the lancet cartridge is appropriate for preventing contamination and the like.

In such lancet cartridges, the lancet is ordinarily housed in the lancet holder, and hence it is difficult to visually check whether the lancet cartridge is a used one or not. In order to solve this problem, the lancet cartridge disclosed in WO 2009/041110 is configured in such a manner that when fitted to the pricking instrument, a small projection provided in the lancet becomes exposed through a slit that is provided in the lancet holder. It becomes possible thereby to check visually, from outside, whether the lancet cartridge is a used one or not.

However, the abovementioned conventional technology leaves room for improvement as regards the features below.

In a conventional lancet cartridge, first of all, the small protrusion exposed on the side face of the lancet holder is of reduced size, and hence it is not found that it is possible to visually check, from outside and in an easy manner, whether the lancet cartridge is a used one or not. In the conventional lancet cartridge, secondly, the lancet and the lancet holder are formed integrally with each other. Therefore, it is not possible to replace a lancet holder by another lancet holder of dissimilar shape, in order to secure a body fluid amount that is sufficient for measurement, as in the pricking instruments disclosed in Japanese Patent Application Publication No. 2005-046612 and Japanese Patent Application Publication No. 2004-237089.

SUMMARY OF THE INVENTION

It is a problem of the present invention, which was arrived at in the light of the above considerations, to provide, firstly, a lancet cartridge such that it is possible to visually check from outside, in an easy manner, whether the lancet cartridge is a used one or not, and to provide, secondly, a lancet cartridge in which the shape of the leading end of a lancet holder can be easily modified, so that a body fluid amount that is sufficient for measurement can be secured as a result.

In order to solve the above problems, the present invention relies on the following technical means.

A lancet cartridge, provided with: a lancet that moves along a pricking track in a pricking direction and that has a pricking member having a leading end section for pricking skin, and a main body section to which a rear end section of the pricking member is fixed; and a lancet holder that accommodates the lancet and that has a first pricking opening at a leading end, the lancet cartridge further having: a skin contact section, held in the interior of the lancet holder, and having a second pricking opening, wherein the first pricking opening is formed to a size such that the skin contact section can be accommodated therein, the lancet cartridge being configured so that when the skin contact section is pressed in the pricking direction, the skin contact section is accommodated in the first pricking opening, and the leading end section of the pricking member protrudes through the second pricking opening.

In the above configuration, the skin contact section is accommodated in the first pricking opening by the point in time at which pricking preparation is over. The skin contact section is large enough to be visible from outside. Accordingly, this allows discriminating easily whether the lancet cartridge according to the present invention has already been used or not.

In a preferred embodiment of the present invention, there are further provided: a protective section that is connected to the skin contact section and that covers the leading end section of the pricking member; and a coupling section that connects the protective section and the main body section so as to cover the periphery of the pricking member; wherein when the protective section is pressed in the pricking direction together with the skin contact section, in a state where the main body section is fixed to the lancet holder, the coupling section breaks and the protective section separates from the main body section, and moreover the leading end section of the pricking member becomes exposed, and subsequently when the protective section and the skin contact section are pressed in the pricking direction, the protective section moves off the pricking track of the pricking member, and the second pricking opening is disposed on the pricking track.

In the above configuration, the skin contact section is accommodated in the first pricking opening by the point in time at which pricking preparation is over. The skin contact section is large enough to be visible from outside. Accordingly, this allows discriminating easily whether the lancet cartridge according to the present invention has already been used or not. Also, the leading end section of the pricking member can protrude through the second pricking opening, without the protective section standing in the way.

In a preferred embodiment of the present invention, the skin contact section can be removed from the first pricking opening and the leading end section of the pricking member protrudes through the first pricking opening in a case where the skin contact section is removed.

In the above configuration, it becomes possible to easily modify the shape of the leading end of the lancet holder that is pressed against the skin of the blood sampling subject. As a result, blood can be appropriately collected at a plurality of dissimilar collection sites, and there can be secured a sufficient body fluid amount for measurement. Also, the leading end section of the pricking member protrudes through the first pricking opening in a case where the skin contact section is removed. For instance, the first pricking opening is formed to be relatively larger than the second pricking opening. Accordingly, the first pricking opening enables the skin of the blood sampling subject to be thrust deeper into the lancet holder than is the case in the second pricking opening. As a result, the leading end section of the pricking member pricks the skin at a deeper point, and a greater amount of body fluid can be collected than when using the second pricking opening. Thus, a sufficient body fluid amount for measurement can be secured by selecting the first pricking opening or the second pricking opening, as the case may require.

In a preferred embodiment of the present invention, the skin contact section or the protective section has a lug section to be gripped upon the removal.

In the above configuration, the skin contact section can be easily removed through gripping of the lug section. This makes for easy changeover from the second pricking opening to the first pricking opening.

In a preferred embodiment of the present invention, a slit is provided in the lancet holder, and the lug section protrudes through the slit when the skin contact section or the protective section is pressed in the pricking direction.

Erroneous operation when the lancet cartridge is not yet in use can be prevented thanks to above configuration.

In a preferred embodiment of the present invention, the skin contact section or the protective section has a cleavable weak section; such that the skin contact section can be removed by cleaving of the weak section.

The above configuration allows easily modifying, through simple cleavage of the weak section, the shape of the leading end of the lancet holder through which there protrudes the leading end section of the pricking member. As a result, the size of the pricking opening can be modified, the leading end of the lancet holder can be imparted with a shape according a plurality of dissimilar collection sites, and the body fluid can be appropriately collected in an amount sufficient for measurement.

In a preferred embodiment of the present invention, the skin contact section is formed of a lamination of a plurality of skin contact sections stacked in the pricking direction and the second pricking opening is formed so as to become smaller as the skin contact sections are disposed closer to the leading end, such that the size of the second pricking opening can be selected by sequentially cleaving the skin contact sections from a skin contact section on the leading end side.

The above configuration allows selecting a skin contact section having an appropriate size of the second pricking opening, as the case may require. The collection amount of body fluid can be finely adjusted as a result.

In a preferred embodiment of the present invention, the skin contact section is formed of a lamination of a plurality of skin contact sections stacked in the pricking direction, the skin contact sections having dissimilar shapes according to pricking sites.

The above configuration allows easily modifying the shape of the leading end of the lancet holder to a shape that conforms to the shape of the pricking site. As a result, the body fluid can be appropriately collected at a plurality of dissimilar collection sites, and there can be secured a sufficient body fluid amount for measurement.

In a preferred embodiment of the present invention, the skin contact section is formed of a plurality of plate-like members plurally partitioned by the weak section so as to surround the second pricking opening, in a plan view, such that the size of the second pricking opening can be selected by sequentially cleaving the plurality of plate-like members from a plate-like member on the inward side.

In the above configuration the size of the second pricking opening can be adjusted in stages through removal of the plate-like members. The collection amount of body fluid can be finely adjusted as a result.

In a preferred embodiment of the present invention, the skin contact section is shaped as a spiral centered on the second pricking opening, and the weak section is formed at a predetermined location of the spiral, such that the size of the second pricking opening can be selected by sequentially cleaving weak sections from a weak section on the inward side of the spiral.

In the above configuration, the size of the second pricking opening can be adjusted in stages through sequential removal of the spiral portion from the center. The collection amount of body fluid can be finely adjusted as a result.

Other features and advantages of the present invention will become more apparent from the description of embodiments of the invention set forth below with reference to accompanying drawings.

DESCRIPTION OF THE PREFERRED EMBODIMENTS

Preferred embodiments of the present invention are explained next with reference to accompanying drawings.

FIG. 1 to FIG. 4 illustrate one example of a lancet cartridge in which the present invention is used. The purpose of a lancet cartridge A1, which is used by being fitted to a pricking instrument 1, is to collect blood, as the measurement target of a compact blood glucose monitor (not shown), from a fingertip or the like. The lancet cartridge A1 may be used by diabetes patients by themselves or in hospitals.

Figure 1:
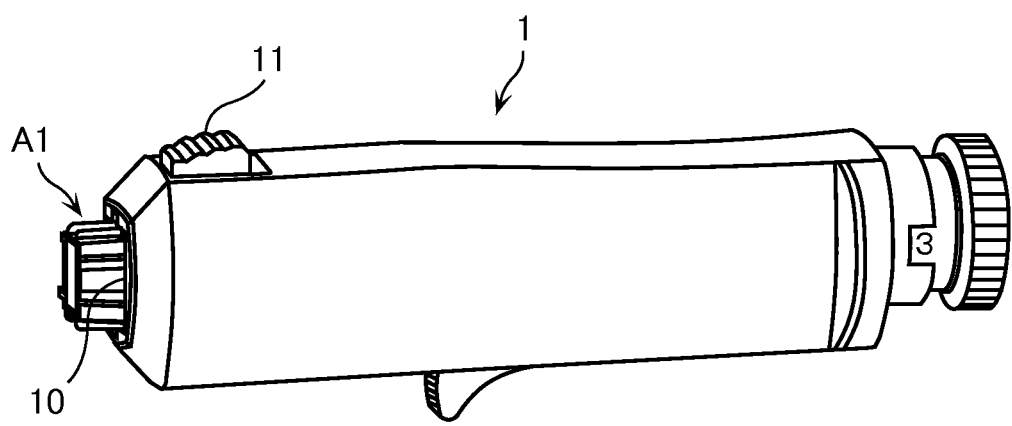
FIG. 1 is a perspective-view diagram illustrating a state in which a lancet cartridge according to the present invention is fitted to a pricking instrument.

As FIG. 1 shows, the lancet cartridge A1 is used by being fitted to the pricking instrument 1. The pricking instrument 1 comprises, for instance, a fitting section 10 and an eject button 11. A pricking mechanism (not shown) is provided in the interior. The fitting section 10 is a portion at which the lancet cartridge A is fitted. The eject button 11 is a button used upon ejection of a below-described lancet 3. To prepare ejection in the process whereby the lancet cartridge A1 is fitted to the pricking instrument 1, a protective cap removal member (not shown), which is a part of the pricking mechanism, and a plunger (not shown) are thrust into the interior of the lancet cartridge A1. In the interior of the pricking instrument 1, meanwhile, ejection is prepared, for instance, through build-up of an elastic force through compression of a spring for pricking (not shown).

Figure 2:
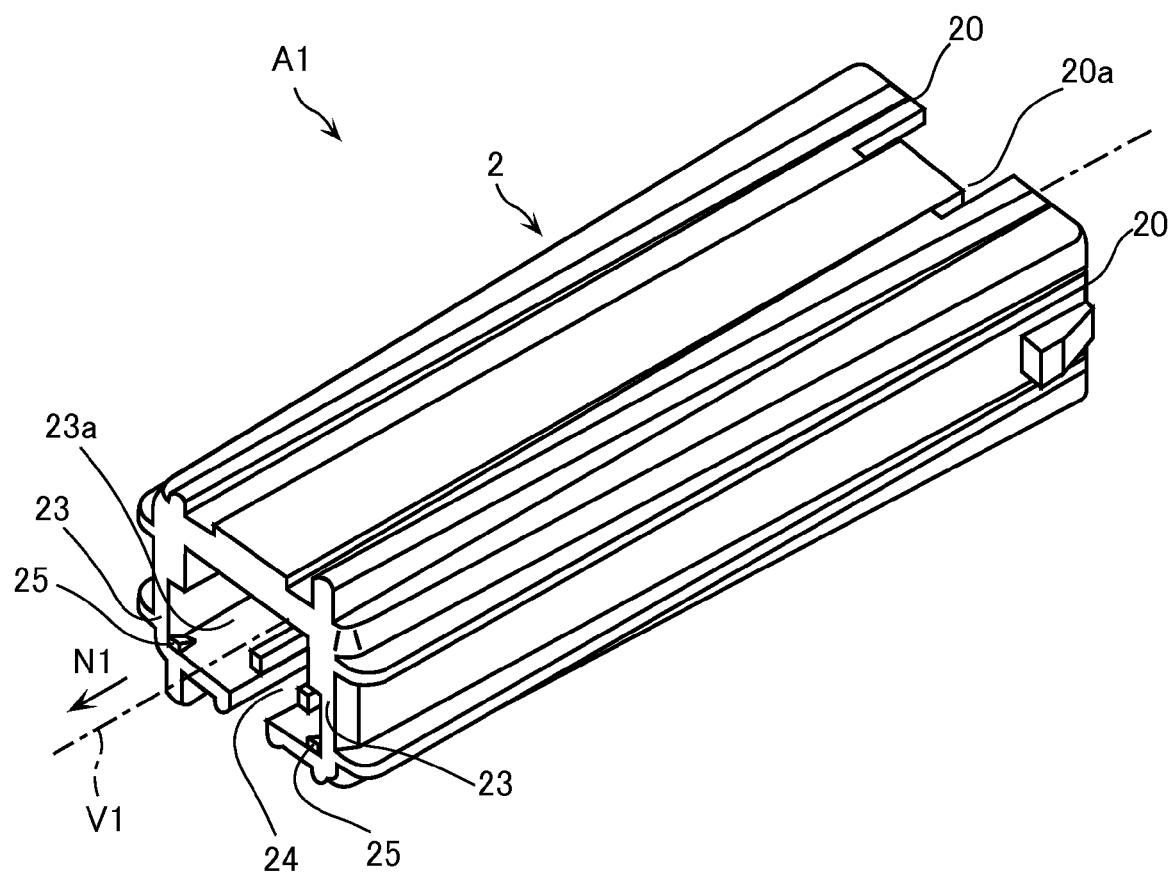
FIG. 2 is an overall perspective-view diagram depicting the lancet cartridge illustrated in FIG. 1.
Figure 3:
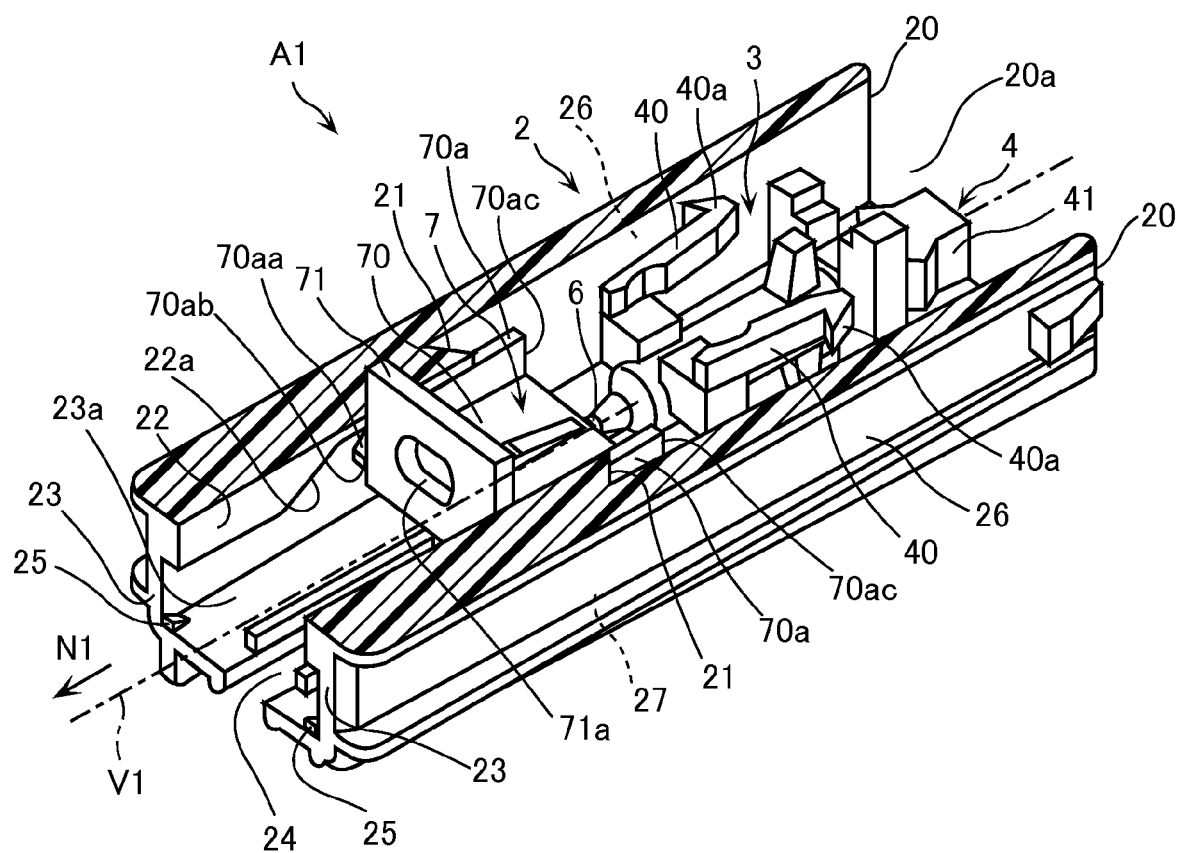
FIG. 3 is a cross-sectional perspective-view diagram depicting the interior of the lancet cartridge illustrated in FIG. 1.

As illustrated in FIG. 2 and FIG. 3, the lancet cartridge A1 is provided with a lancet holder 2 and a lancet 3. In the explanation hereafter, directions such as the vertical direction and the like correspond to directions as depicted in the drawings.

The purpose of the lancet holder 2 is to house and hold, in the interior thereof, the below-described lancet 3. After use, the lancet 3 is discarded while housed in the lancet holder 2. The lancet holder 2 is formed by injection molding using a synthetic resin as a material. Specific examples of the synthetic resin include, for instance, polyethylene, polypropylene and the like. The color of the lancet holder 2 is different from that of the lancet 3. The lancet holder 2 is colored in light grey, while the lancet 3 is colored in pink. Thereby, the position of the lancet 3 in the lancet holder 2 can be readily checked visually from the outside. The combination of colors of the lancet holder 2 and the lancet 3 may be any combination, so long as the different colors can be easily told apart from each other. As illustrated in FIG. 3, the lancet holder 2 comprises a rear end opening 20a, stopper sections 21, slope sections 22, a leading end 23, a first pricking opening 23a, a slit 24, and protrusions 25.

The rear end opening 20a is formed at a rear end 20 of the lancet holder 2. The lancet 3 is inserted through the rear end opening 20a during assembly of the lancet cartridge A1. The abovementioned protective cap removal member and plunger are thrust into the lancet holder 2, through the rear end opening 20a, during fitting of the lancet cartridge A1 to the pricking instrument 1.

The stopper sections 21 are portions against which there abut abutting sections 40a of wing sections 40 that are provided in a main body section 4 of the lancet 3, as described below. The pair of stopper sections 21 is provided on the inner face of side wall sections 26 at the left and right of the lancet holder 2. The motion of a pricking member 5 in the pricking direction N1, after use as described below, is limited through abutting of the abutting sections 40a against the stopper sections 21. As a result, a tip 5a of the pricking member 5 is prevented from becoming exposed to the exterior through a first pricking opening 23a or a second pricking opening 71a that are described below.

The pair of slope sections 22 is provided, contiguously to the pair of stopper sections 21, on the inner face of the side wall sections 26 of the lancet holder 2, facing in the pricking direction N1. The slope sections 22 have respective slope faces 22a that tilt downward as they extend in the pricking direction N1. A below-described protective cap 7 of the lancet 3 moves along the slope faces 22a when pressed from behind.

The leading end 23 is a portion that is pressed against the skin of the blood sampling subject. The below-described first pricking opening 23a is formed at substantially the central section of the leading end 23. The peripheral section of the first pricking opening 23a is formed planarly at the leading end 23. Needless to say, the shape of the peripheral section of the first pricking opening 23a may be any shape, so long as blood sampling can take place appropriately, and may be a curved shape that conforms to the blood sampling site, for instance, the fingertips, palms, forearms, earlobes and the like.

The first pricking opening 23a is formed at the leading end 23 of the lancet holder 2, as described above. The first pricking opening 23a is formed to such a size as allows accommodating the below-described skin contact section 71 that is provided in the protective cap 7 of the lancet 3. As described below, the tip 5a of the pricking member 5 is configured so as to protrude through the first pricking opening 23a when the protective cap 7 is removed from the lancet holder 2.

The slit 24 is provided at a bottom wall section 27 in the lancet holder 2, in the vicinity of the leading end 23. The purpose of the slit 24 is to enable a below-described lug section 70b, which is provided in the protective cap 7 of the lancet 3, to protrude outside the lancet holder 2.

The protrusions 25 are provided on the inner face of the bottom wall section 27 of the lancet holder 2 in the vicinity of the leading end 23. The purpose of the protrusions 25 is to prevent the protective cap 7 from coming off out of the lancet holder 2 via the first pricking opening 23a, through locking of the protective cap 7 that has moved up to the vicinity of the leading end 23.

The purpose of the lancet 3, which is housed inside the lancet holder 2, is to prick the skin, for instance of the fingertip or the like, of the blood sampling subject. The lancet 3 is molded by insert molding, wherein the below-described pricking member 5 is embedded in a synthetic resin material. Specific examples of the synthetic resin include, for instance, polyethylene, polypropylene or the like. As illustrated in FIG.

Figure 4:
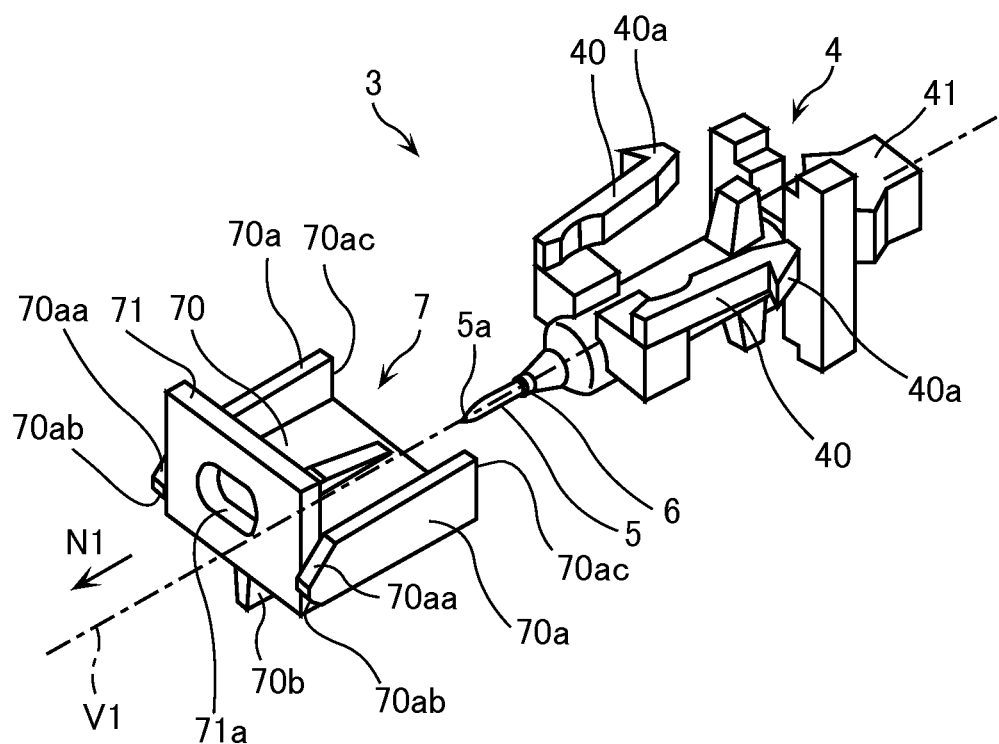
FIG. 4 is a perspective-view diagram depicting a state in which a protective cap is removed from a lancet of the lancet cartridge illustrated in FIG. 1.

3 and FIG. 4, the lancet 3 has a main body section 4, a pricking member 5, a coupling section 6 and the protective cap 7.

The main body section 4, to which the rear end section of the pricking member 5 is fixed, moves along the pricking track V1 in the pricking direction N1, to prick the skin of the test subject. The main body section 4 comprises the wing sections 40 and an engagement section 41.

The wing sections 40 are configured in such a manner that, after pricking, the tip 5a of the pricking member 5 is exposed through the first pricking opening 23a or the below-described second pricking opening 71a. The pair of wing sections 40 is provided in such a manner the wing sections 40 spread gradually outward in the rearward direction, symmetrically with respect to the pricking member 5 as the center axis. Displacement of the pricking member 5 in the pricking direction N1 is restricted through abutting of the pair of wing sections 40 against the stopper sections 21. At the leading end thereof, the pair of wing sections 40 has abutting sections 40a that abut the stopper sections 21. The wing sections 40 are formed to be deformable, such that during pricking, the wing sections 40 are thrust inward by the protective cap removal member of the pricking instrument 1 that is thrust into the lancet holder 2 through the rear end opening 20a. As a result, the abutting sections 40a do not abut the stopper sections 21, and the main body section 4 can move up to the leading end 23. The wing sections 40 spread out again, by virtue of an outward elastic force, when the lancet cartridge A1 is removed from the pricking instrument 1.

The engagement section 41 is a portion of the main body section 4 that engages with the plunger in the pricking instrument 1 when the lancet cartridge A1 is fitted to the pricking instrument 1. The pricking instrument 1 can eject as a result the main body section 4 in the pricking direction N1.

The purpose of the pricking member 5 is to protrude outside the lancet holder 2, through the first pricking opening 23a or the second pricking opening 71a, and to make an incision in the skin of the subject for sample collection. The pricking member 5 is made of metal. The specific material of the pricking member 5 is stainless steel. The pricking member 5 may be any member, so long as it allows appropriate incisions to be made on the skin of the subject for sample collection, and may be formed out of a metal other than stainless steel, or out of a synthetic resin. The pricking member 5 may be shaped in the form of a needle or a blade. The rear end section of the pricking member 5 is fixed to the main body section 4. The pricking member 5 is configured so as to slide along the pricking track V1 at all times. The tip 5a of the pricking member 5 is sharpened by polishing. The tip 5a of the pricking member 5 is covered by the protective cap 7, by way of the below-described coupling section 6.

The purpose of the coupling section 6, which is a member interposed between the main body section 4 and the protective cap 7, is to keep the pricking member 5 sterile. The coupling section 6 is configured so as to break when the protective cap 7 is pressed from behind by the protective cap removal member of the pricking instrument 1. The coupling section 6 is formed to be thin-walled around the pricking member 5, so as to break more readily.

The purpose of the protective cap 7 is to prevent bending of the cutting edge of the pricking member 5 and to preserve sterility, by covering the cutting edge of the pricking member 5. The protective cap 7 comprises a protective section 70 and a skin contact section 71. The protective section 70 of the protective cap 7 is connected to the main body section 4 via the coupling section 6, and covers the cutting edge of the pricking member 5. The protective section 70 is a substantially planar member that extends, on the left and right, with the pricking member 5 as a center axis. The protective section 70 is positioned on the pricking track V1 of the pricking member 5. Therefore, the pricking member 5 cannot move in the pricking direction N1, on the pricking track V1, even with the protective section 70 removed. The protective section 70 has a pair of sledge sections 70a on both side faces. The purpose of the sledge sections 70a is to enable the protective cap 7 to be appropriately held in, and move smoothly along, the lancet holder 2. The sledge sections 70a have respective pressing sections 70ac for enabling the protective cap removal member of the pricking instrument 1 to press the protective cap 7 in the pricking direction N1. The protective section 70 and the skin contact section 71 become pressed in the pricking direction N1 when the pressing sections 70ac are pressed from behind. When the protective cap 7 is pressed from behind, with the main body section 4 fixed in the lancet holder, the coupling section 6 breaks, and the protective cap 7 separates from the main body section 4 and moves in the pricking direction N1. Thereupon, upper tapered sections 70aa of the sledge sections 70a move along the slope faces 22a, and, accordingly, the protective cap 7 moves obliquely downward, in the pricking direction N1. The protective section 70 moves thus off the pricking track V1 of the pricking member 5.

The skin contact section 71 is a plate-like member erected at the leading end of the protective section 70, in a direction that intersects the pricking direction N1. More specifically, the skin contact section 71 is provided so as to be perpendicular to the pricking direction N1. The skin contact section 71 becomes accommodated in the first pricking opening 23a when the protective cap 7 moves in the pricking direction N1. The second pricking opening 71a is provided at substantially the central section of the skin contact section 71. At the time before use, i.e. before fitting to the pricking instrument 1, the second pricking opening 71a is positioned above the pricking track V1, spaced apart from the latter. The second pricking opening 71a is configured in such a manner so as to reach a position that is crossed by the pricking track V1 when the protective cap 7 moves up to the position of the first pricking opening 23a as the protective cap 7 moves along the slope faces 22a. By being now free of obstacles, the tip 5a of the pricking member 5 can move along the pricking track V1 in the pricking direction N1, and can protrude through the second opening 71a. A peripheral section of the second pricking opening 71a of the skin contact section 71 is formed to a planar shape. Needless to say, the shape of the peripheral section of the second pricking opening 71a may be any shape, so long as blood sampling can take place appropriately, and may be a curved shape that conforms to the blood sampling site, for instance, the fingertips, palms, forearms, earlobes and the like.

As illustrated in FIG. 4, the lug section 70b is provided at the lower face the protective section 70. At a time before use, the lug section 70b supports the protective cap 7 in the lancet holder 2. The lancet cartridge A1 is configured in such a manner that the lug section 70b protrudes out of the lancet holder 2 through the slit 24, when the lancet cartridge A1 is fixed to the pricking instrument 1 and the protective cap 7 moves to the vicinity of the leading end 23. The protective cap 7 is prevented from coming off the first pricking opening 23a through engagement of bottom tapered sections 70ab of the sledge sections 70a with the protrusions 25.

The engagement between the bottom tapered sections 70ab and the protrusions 25 can be released, such that the protective cap 7 can be removed from the lancet holder 2, through gripping of the lug section 70b, and sliding of the lug section 70b in the pricking direction N1 along the slit 24. In this case, the pricking member 5 protrudes through the first pricking opening 23a.

The operation of the lancet cartridge A1 is explained next with reference to FIG. 5 to FIG. 9.

Figure 5:
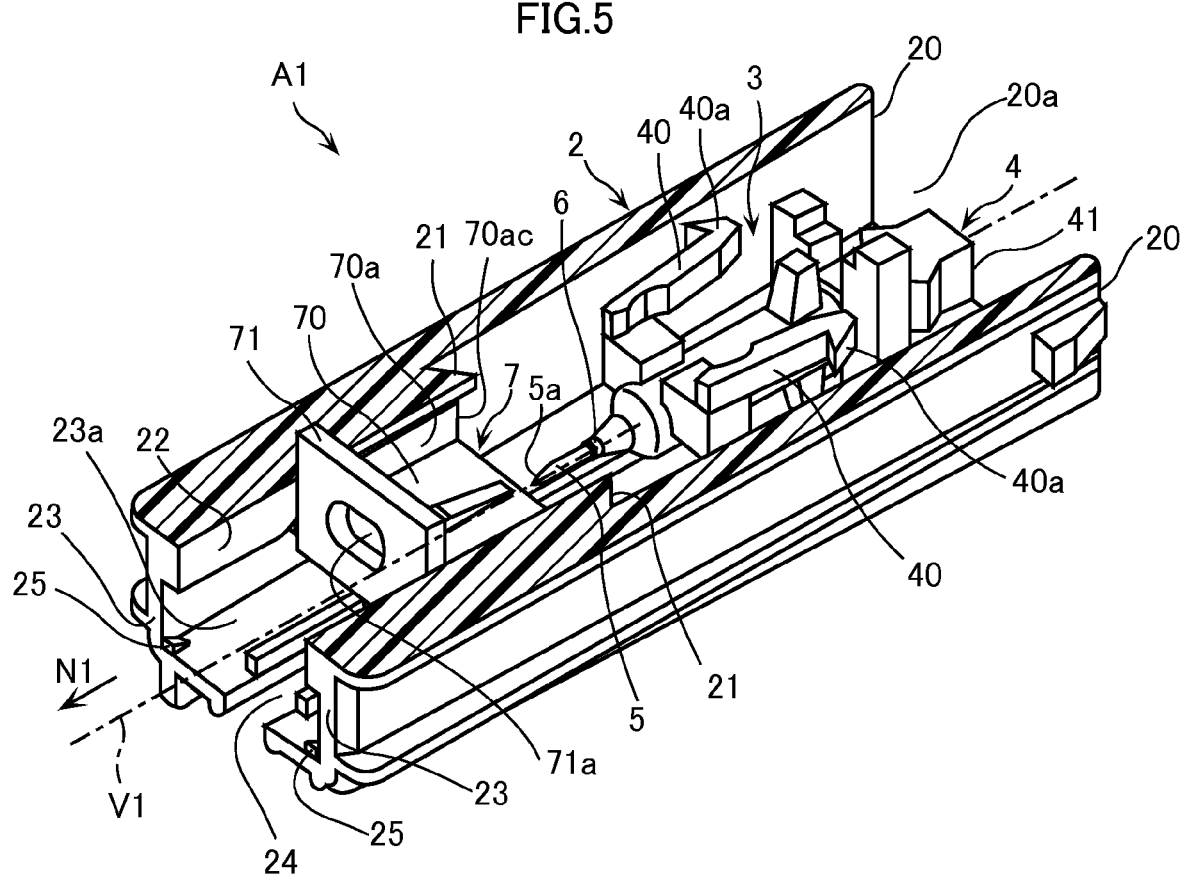
FIG. 5 is a cross-sectional perspective-view diagram for explaining the operation of the lancet cartridge illustrated in FIG. 1.

Firstly, when the lancet cartridge A1 is inserted in the fitting section 10 of the pricking instrument 1, the protective cap removal member thrusts into the lancet cartridge A1, and presses the pressing sections 70ac of the lancet 3. As a result of this pressing, the protective cap 7 moves in the pricking direction N1, as illustrated in FIG. 5. At this time, the main body section 4 remains fixed in the lancet holder 2, and hence the coupling section 6 breaks and the tip 5a of the pricking member 5 becomes exposed. Meanwhile, although not illustrated in the figures, the plunger of the pricking instrument 1 engages with the engagement section 41. At this point in time, the protective section 70 is on the pricking track V1 of the pricking member 5, and the second pricking opening 71a is off the pricking track V1.

Figure 6:
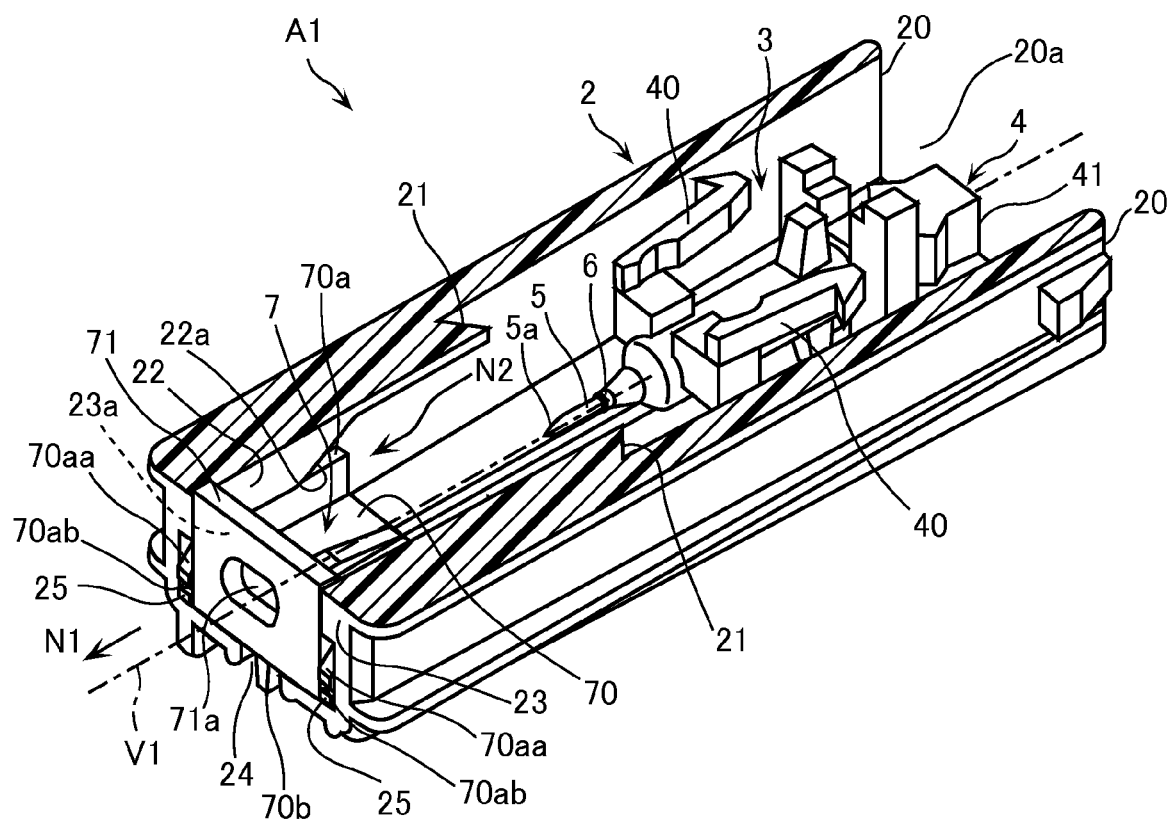
FIG. 6 is a cross-sectional perspective-view diagram for explaining the operation of the lancet cartridge illustrated in FIG. 1.

Next, when the protective cap 7 is further pressed in the pricking direction N1, as illustrated in FIG. 6, the skin contact section 71 becomes accommodated in the first pricking opening 23a, and plugs the first pricking opening 23a. The upper tapered sections 70aa slide herein along the slope faces 22a, and hence the protective cap 7 moves obliquely downward as denoted by arrow N2. As a result, the protective section 70 moves off the pricking track V1 of the pricking member 5, while the second pricking opening 71a moves along the pricking track V1. Herein, the protective cap 7 is prevented from coming off the lancet holder 2 through engagement of the bottom tapered sections 70ab of the sledge sections 70a, in the protective cap 7, with the protrusions 25. The lug section 70b protrudes out of the lancet holder 2 through the slit 24.

Figure 7:
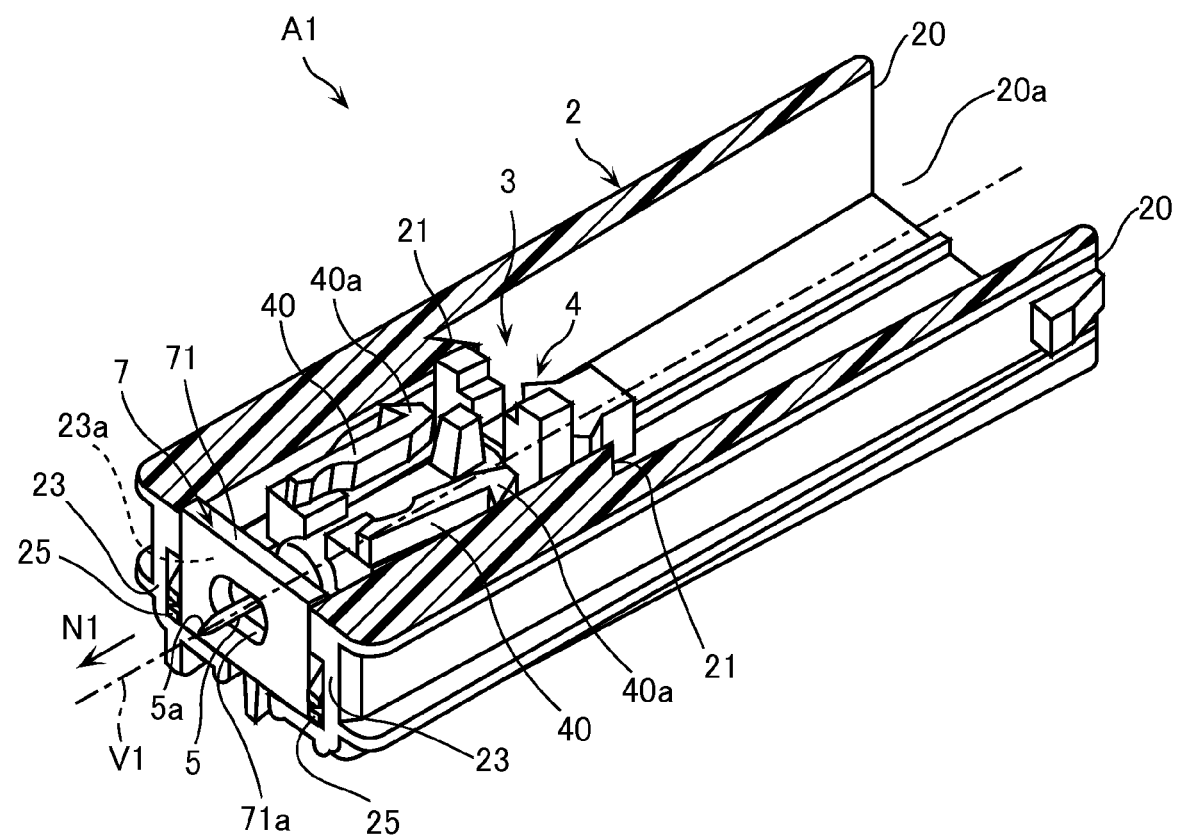
FIG. 7 is a cross-sectional perspective-view diagram for explaining the operation of the lancet cartridge illustrated in FIG. 1.

When the eject button 11 of the pricking instrument 1 is pressed next, the plunger is ejected by virtue of the elastic force of the abovementioned spring for pricking. As a result, the main body section 4 moves in the pricking direction N1, as illustrated in FIG. 7. The pricking member 5 that is fixed to the main body section 4 moves also along the pricking track V1 in the pricking direction N1. As a result, the tip 5a of the pricking member 5 protrudes through the second pricking opening 71a, and the skin of the blood sampling subject is pricked. At this time, the pair of wing sections 40 is thrust inward by the protective cap removal member of the pricking instrument 1, and the main body section 4 is brought to a state of being capable of moving in the pricking direction N1, without abutting of the abutting sections 40a against the stopper sections 21.

Figure 8:
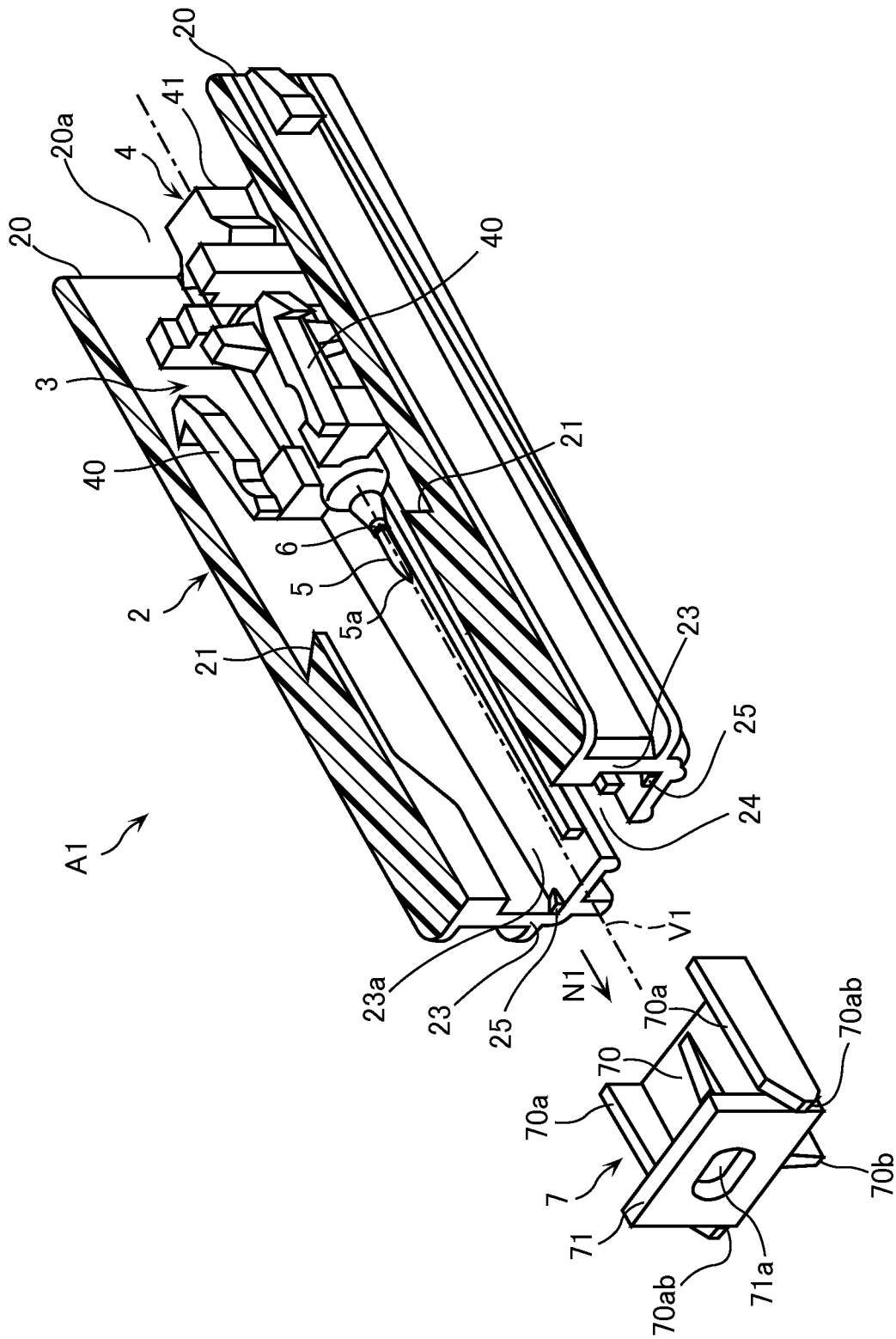
FIG. 8 is a cross-sectional perspective-view diagram for explaining the operation of the lancet cartridge illustrated in FIG. 1.

In a case where an appropriate blood sampling amount cannot be obtained with the tip 5a of the pricking member 5 protruding through the second pricking opening 71a, the protective cap 7 is removed off the leading end 23 of the lancet holder 2 in a state where the lancet cartridge A1 is fitted to the pricking instrument 1, as illustrated in FIG. 8. Specifically, the lug section 70b is gripped and caused to slide in the pricking direction N1 along the slit 24; thereby, the lock between the protrusions 25 and the bottom tapered sections 70ab of the sledge sections 70a is lifted, and the protective cap 7 is removed off the lancet holder 2. As a result, the tip 5a of the pricking member 5 protrudes now through the first pricking opening 23a.

Figure 9:
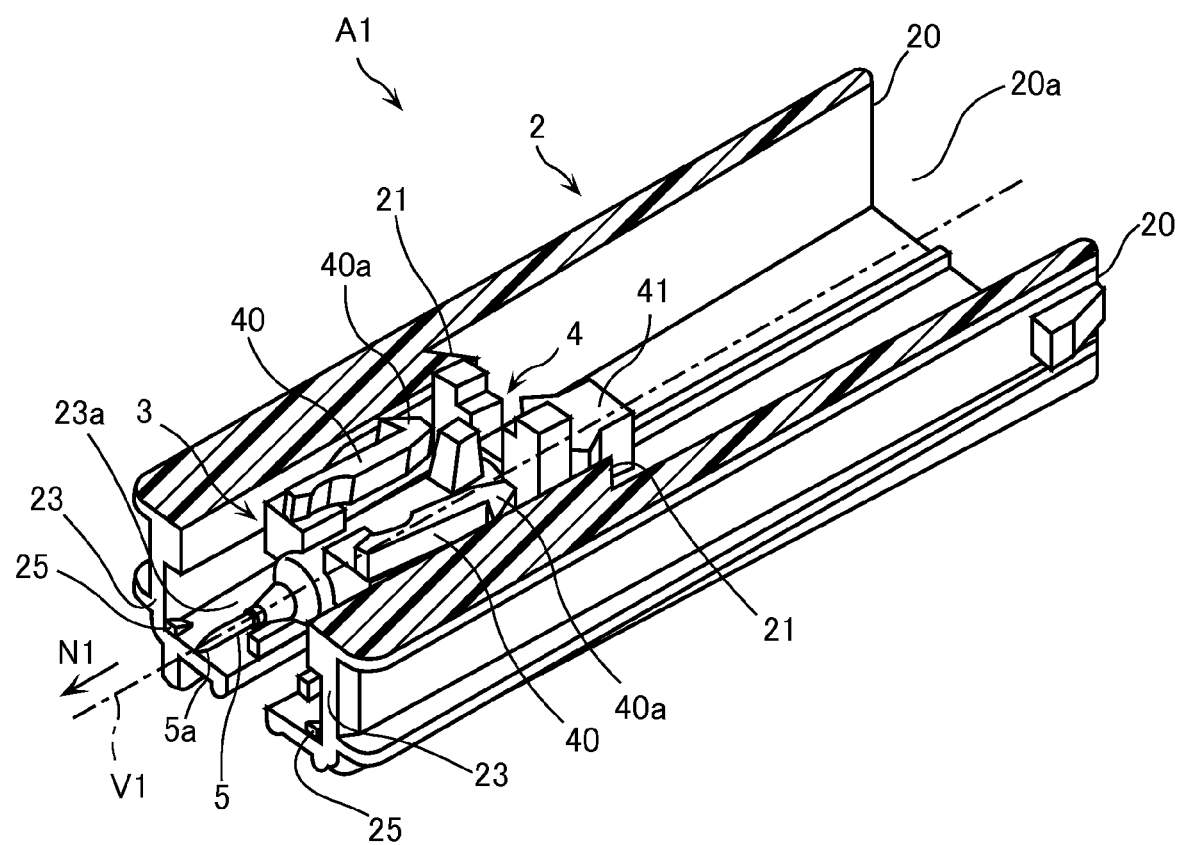
FIG. 9 is a cross-sectional perspective-view diagram for explaining the operation of the lancet cartridge illustrated in FIG. 1.

As illustrated in FIG. 9, the main body section 4 moves in the pricking direction N1 when the eject button 11 of the pricking instrument 1 is pressed. The tip 5a of the pricking member 5 protrudes through the first pricking opening 23a and pricks the skin of the blood sampling subject. The first pricking opening 23a is formed to be larger than the second pricking opening 71a, and thus the skin of the blood sampling subject thrusts deeper into the lancet holder 2. The blood sampling amount increases since pricking is accordingly deeper.

During use, the skin contact section 71 of the protective cap 7 in the present embodiment is disposed so as to plug the first pricking opening 23a, as described above. The skin contact section 71 is large enough to be visible from outside. Accordingly, this allows discriminating easily whether the lancet cartridge A1 has already been used or not. Re-use of a used lancet cartridge A1 can therefore be easily prevented. By the point in time at which the pricking preparation is over, the protective section 70 is off the pricking track V1 of the pricking member 5, and the second pricking opening 71a is disposed on the pricking track V1. Therefore, the tip 5a of the pricking member 5 can protrude through the second pricking opening 71a, without the protective section 70 standing in the way.

In the lancet cartridge A1 the lancet holder 2 and the lancet 3 have dissimilar colors. Therefore, it is possible to easily discriminate whether the lancet cartridge is a used one or not.

When the lancet cartridge A1 is in use, firstly the skin contact section 71 moves to the leading end 23 that is pressed against the skin of the blood sampling subject. Accordingly, the likelihood of contamination while not yet in use is low. The lancet cartridge A1 is therefore advantageous in terms of securing hygiene.

The lancet cartridge A1 is configured so that the protective cap 7 can be removed from the lancet holder 2. Therefore, it becomes possible to easily modify the shape of the leading end 23 of the lancet holder 2 that is pressed against the skin of the blood sampling subject. As a result, blood can be appropriately collected at a plurality of dissimilar collection sites, and a blood amount can be secured that is sufficient for measurement. The lancet cartridge is configured in such a manner that, when the protective cap 7 is removed, the tip 5a of the pricking member 5 protrudes through the first pricking opening 23a. For instance, the first pricking opening 23a is formed to be relatively larger than the second pricking opening 71a. Accordingly, the first pricking opening 23a enables the skin of the blood sampling subject to be thrust deeper into the lancet holder 2 than is the case in the second pricking opening 71a. As a result, the tip 5a of the pricking member 5 pricks the skin at a deeper point, and a greater amount of blood can be collected, than when using the second pricking opening 71a. Thus, a sufficient blood amount for measurement can be secured by selecting the first pricking opening 23a or the second pricking opening 71a as the case may require. Therefore, the blood sampling amount can be adjusted in cases where the pricking depth of the pricking instrument 1 cannot be successfully adjusted, even if the lancet cartridge A1 has a mechanism for adjusting the pricking depth.

The protective cap 7 of the lancet cartridge A1 has the lug section 70b for gripping upon removal of the protective cap 7. As a result, the protective cap 7 can be easily removed through gripping of the lug section 70b. This makes for easy changeover from the second pricking opening 71a to the first pricking opening 23a.

The lug section 70b is configured so as to protrude firstly through the slit 24 that is provided in the bottom section 27 of the lancet holder 2 when the lancet cartridge A1 is inserted into the fitting section 10 of the pricking instrument 1. As a result, the protective cap 7 can be easily removed through gripping and sliding of the lug section 70b along the slit 24. Erroneous operation when the lancet cartridge is not yet in use can be thus prevented, since the protective cap 7 is configured in such a manner that the lug section 70b protrudes firstly through the slit 24 when the protective cap 7 is pressed in the pricking direction N1.

Figure 10A:
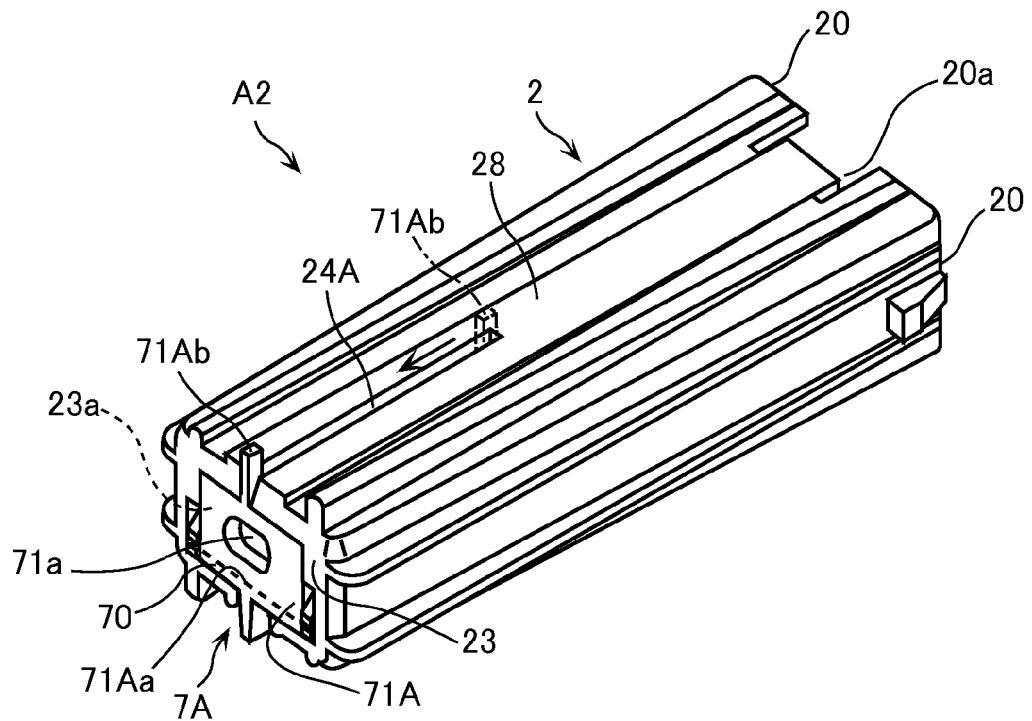
FIG. 10A and FIG. 10B are perspective-view diagrams illustrating another example of a lancet cartridge according to the present invention.
Figure 10B:
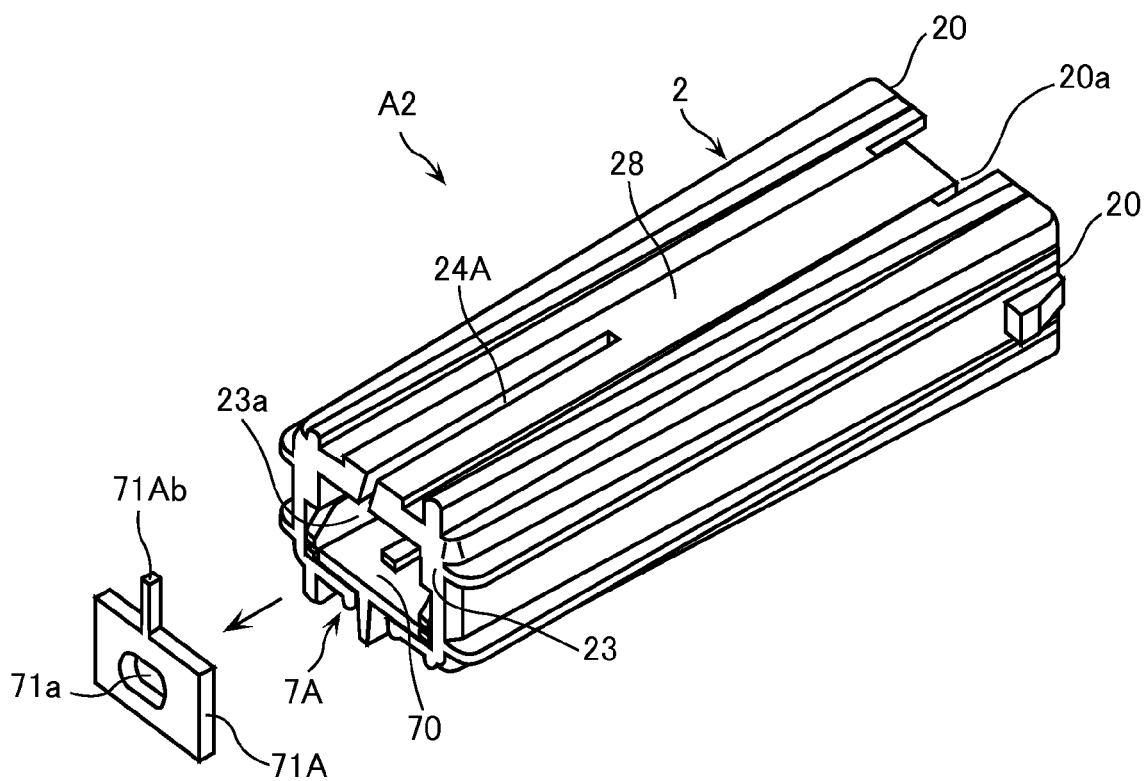

FIG. 10A and FIG. 10B illustrate another embodiment of a lancet cartridge according to the present invention. Identical or similar embodiments in the figures are denoted with reference numerals identical to those of the embodiment above. The same applies to other embodiments below.

The basic configuration of the lancet cartridge A2 is identical to that of the lancet cartridge A1 explained above, but differs as regards of the configuration for removing the skin contact section 71A.

In the lancet cartridge A2, a protective cap 7A comprises a perforation 71Aa and a lug section 71Ab. As illustrated in FIG. 10A, the perforation 71Aa is provided at the boundary between the protective section 70 and the skin contact section 71A. The portion of the perforation 71Aa is less strong than the periphery thereof, so that the former can break easily. The perforation 71Aa corresponds to an example of the weak section of the present invention. The lancet cartridge A2 is provided with the lug section 71Ab on top of the skin contact section 71A. The lug section 71Ab protrudes through a slit 24A that is formed on a top wall section 28 of the lancet holder 2, and the lancet cartridge A2 slides through the slit 24A and moves to the leading end 23 when the lancet cartridge A2 is fitted to the pricking instrument 1. The skin contact section 71A can be cleaved along the perforation 71Aa and can be removed, as illustrated in FIG. 10B, by moving the lug section 71Ab in the direction indicated by the arrow. The first pricking opening 23a that is housed in the protective cap 7A appears thereupon as a result.

The present embodiment allows modifying easily the shape of the leading end 23, of the lancet holder 2, through which there protrudes the tip 5a of the pricking member 5. As a result, the size of the pricking opening can be modified, the leading end 23 of the lancet holder 2 can be imparted with a shape according a plurality of dissimilar collection sites, and blood can be appropriately collected in an amount sufficient for measurement.

Figure 11A:
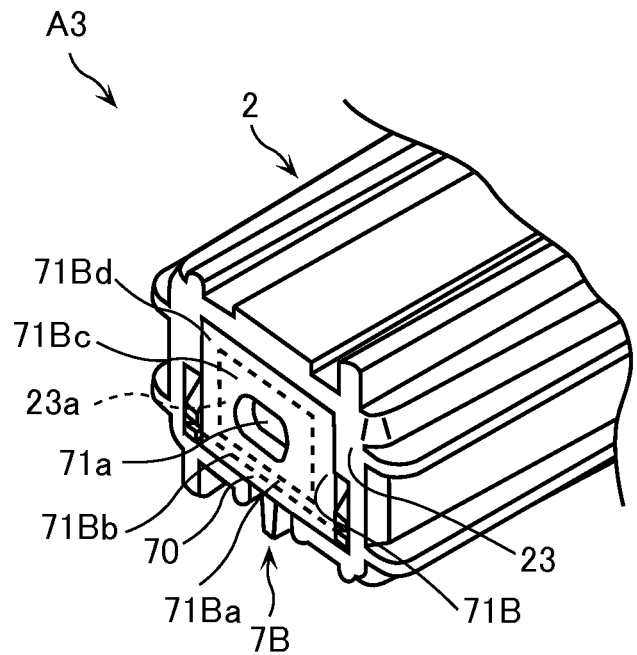
FIG. 11A and FIG. 11B are perspective-view diagrams illustrating another example of a lancet cartridge according to the present invention.
Figure 11B:
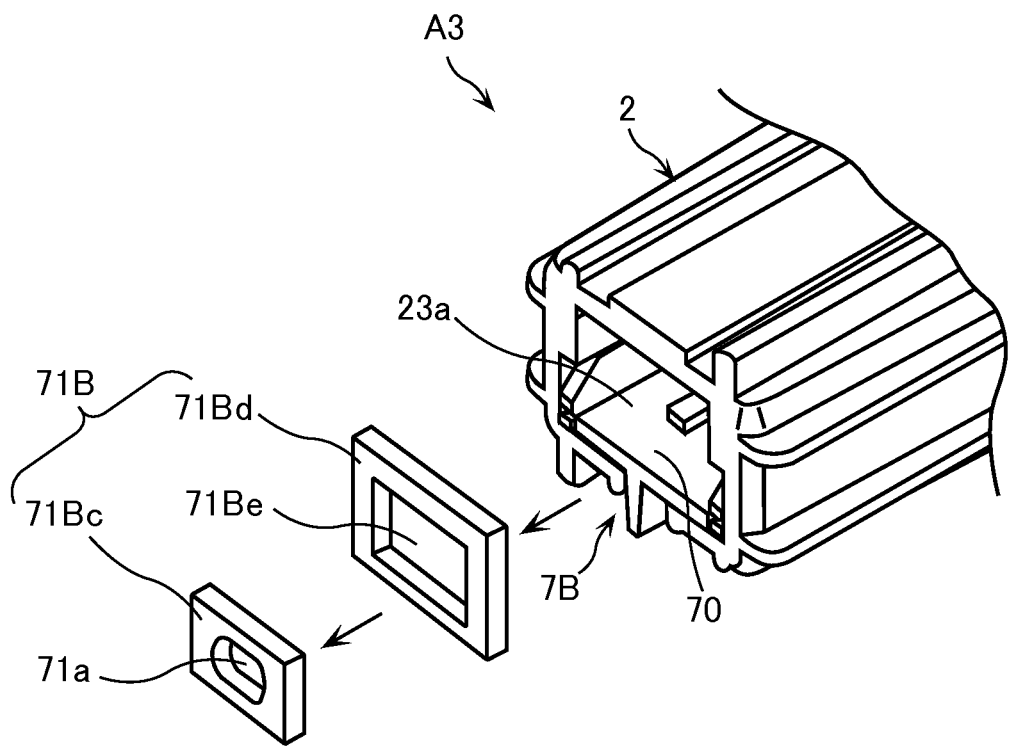

FIG. 11A and FIG. 11B illustrate another embodiment of a lancet cartridge according to the present invention. A lancet cartridge A3 has a configuration for removing a skin contact section 71B that is different from that of the above-described lancet cartridge A1.

In the lancet cartridge A3, as shown in FIG. 11A, the skin contact section 71B of the protective cap 7B is made up of a plurality of plate-like members 71Bc, 71Bd partitioned by perforations 71Ba, 71Bb so as to surround a second pricking opening 71a, in a plan view. The perforations 71Ba, 71Bb correspond to an example of the weak section of the present invention. The plate-like members 71Bc, 71Bd can be sequentially cleaved from the inward side, as illustrated in FIG. 11A and FIG. 11B. Firstly, the plate-like member 71Bc is cleaved along the perforation 71Ba, and is removed. As a result, the second pricking opening 71a is replaced by a second pricking opening 71Be. Next, the plate-like member 71Bd is cleaved along the perforation 71Bb, and is removed, to reveal as a result the first pricking opening 23a.

In the present embodiment, the second pricking openings 71a, 71Be can be selected through sequential removal of the plurality of plate-like members 71Bc, 71Bd. That is, the size of the pricking opening can be adjusted in stages. The collection amount of blood can be finely adjusted as a result.

Figure 12A:
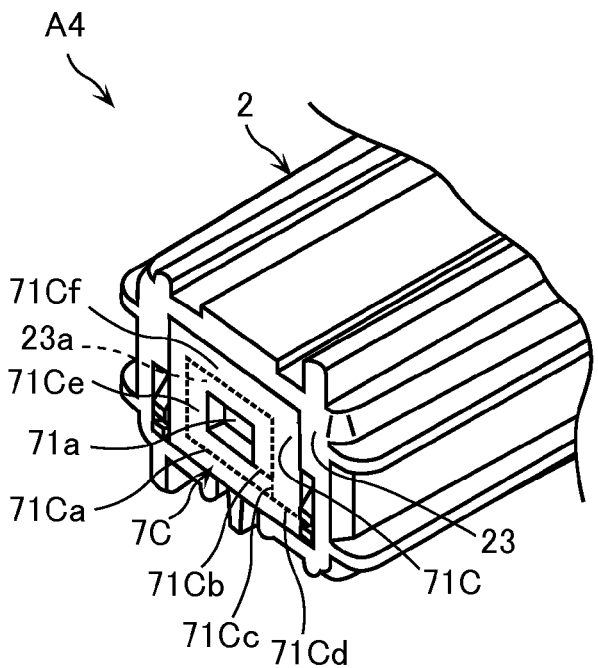
FIG. 12A and FIG. 12B are perspective-view diagrams illustrating another example of a lancet cartridge according to the present invention.
Figure 12B:
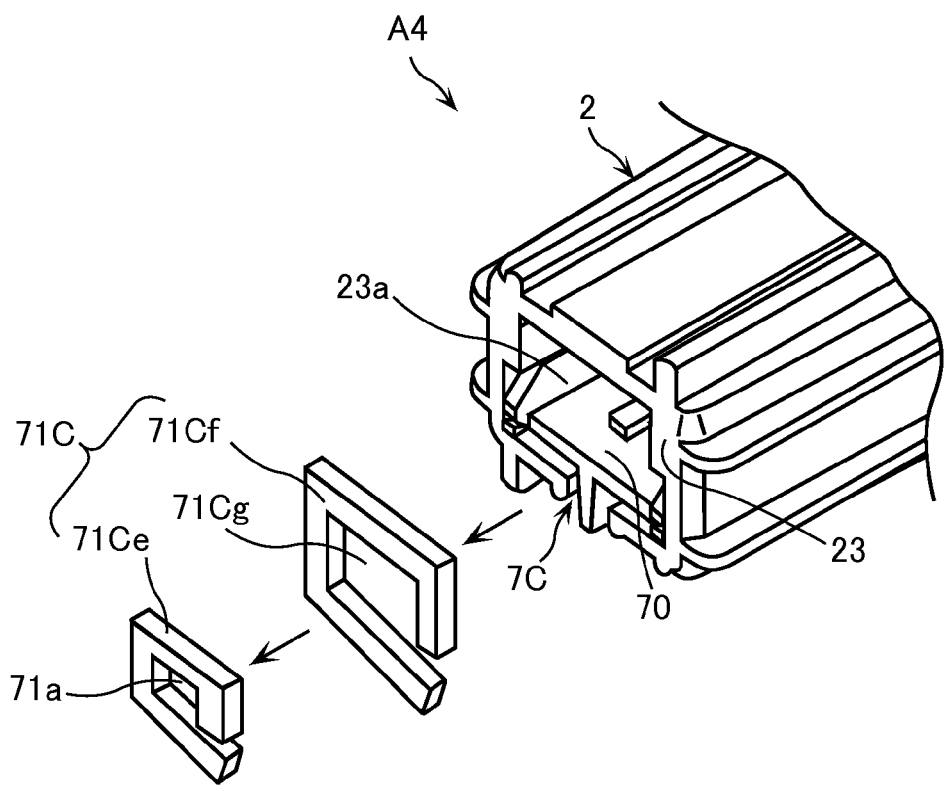

FIG. 12A and FIG. 12B illustrate another embodiment of a lancet cartridge according to the present invention. A lancet cartridge A4 has a configuration for removing a skin contact section 71C that is different from that of the above-described lancet cartridge A1.

As illustrated in FIG. 12A, a skin contact section 71C of a protective cap 7C in the lancet cartridge A4 is shaped as a spiral centered on the second pricking opening 71a. The spiral is formed by a perforation 71Ca. Perforations 71Cb, 71Cc, 71Cd are formed at a predetermined location of the spiral. In the lancet cartridge A4, the size of the second pricking opening is selected in stages through sequential cleaving of the perforations 71Cb, 71Cc, 71Cd, from the inward side of the spiral. The perforations 71Ca, 71Cb, 71Cc, 71Cd correspond to an example of the weak section of the present invention. As illustrated in FIG. 12A and FIG. 12B, firstly, the second pricking opening 71a is replaced by a second pricking opening 71Cg through removal of a fragment 71Ce from the perforation 71Cb up to the perforation 71Cc. Next, a fragment 71Cf is removed through cleaving from the perforation 71Cd up to a perforation (not shown) that is formed at the boundary between the skin contact section 71C and the protective section 70; the first pricking opening 23a is revealed as a result.

In the present embodiment, the size of the second pricking opening can be adjusted in stages through sequential removal of the spiral portion from the center. The collection amount of blood can be finely adjusted as a result.

Figure 13A:
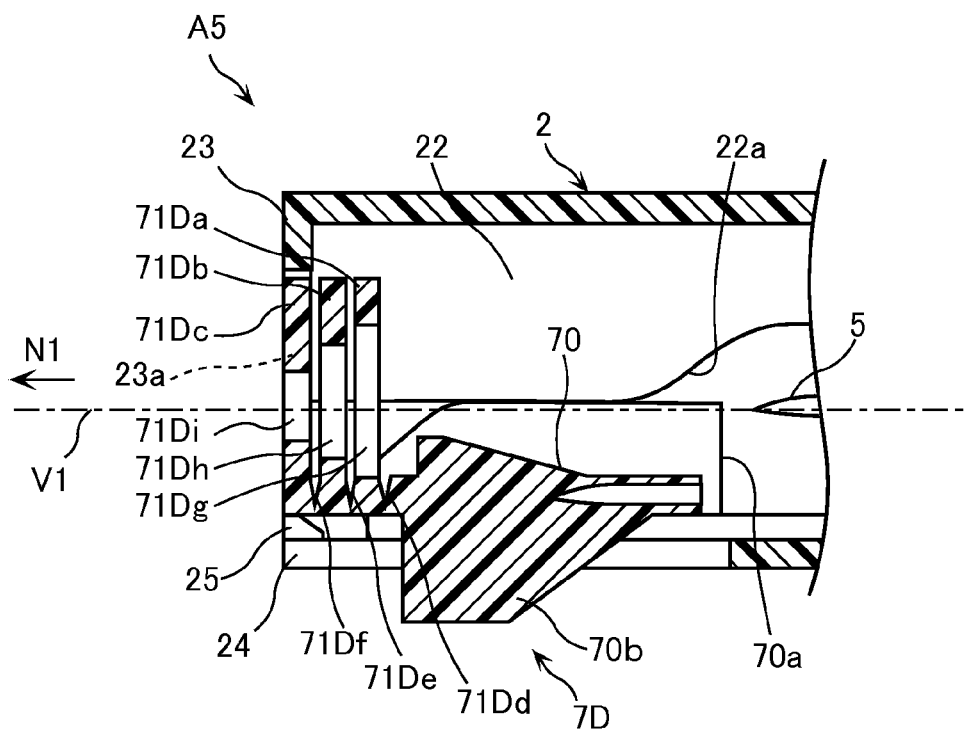
FIG. 13A and FIG. 13B are cross-sectional diagrams illustrating another example of a lancet cartridge according to the present invention.
Figure 13B:
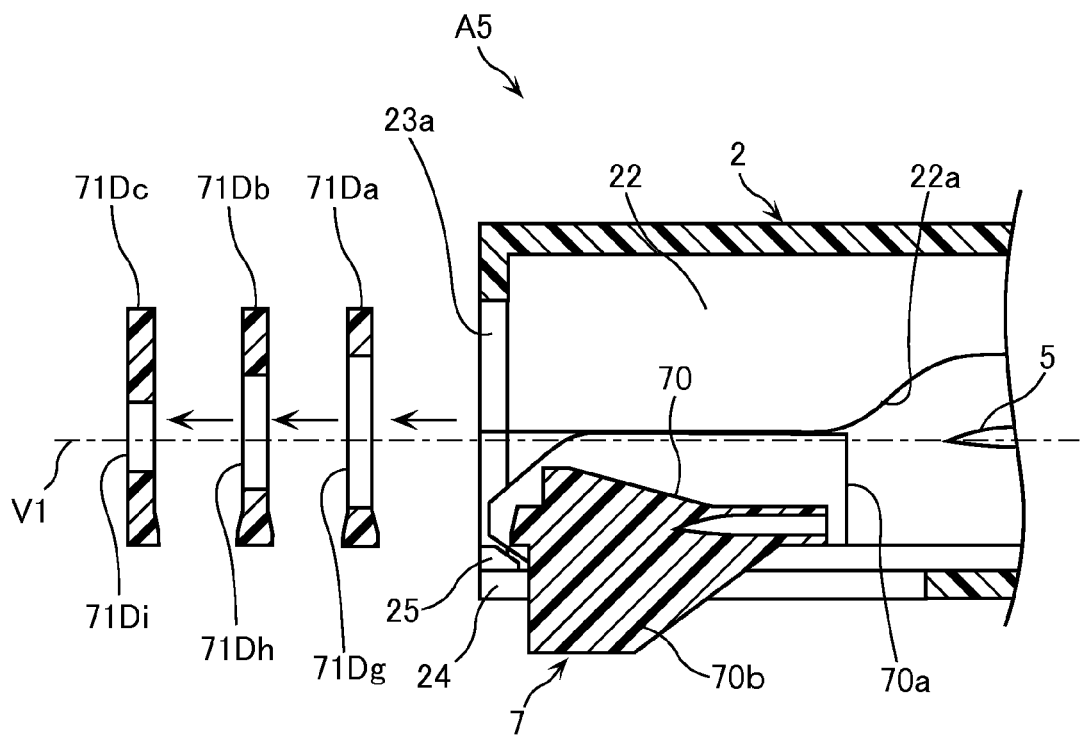

FIG. 13A and FIG. 13B illustrate another embodiment of a lancet cartridge according to the present invention. A lancet cartridge A5 has a configuration for removing skin contact sections 71Da, 71Db, 71Dc that is different from that of the above-described lancet cartridge A1.

As illustrated in FIG. 13A, the lancet cartridge A5 is provided with a protective cap 7D in which a plurality of skin contact sections 71Da, 71Db, 71Dc is stacked in the pricking direction N1. Second pricking openings 71Dg, 71Dh, 71Di of the plurality of skin contact sections 71Da, 71Db, 71Dc are formed so as to become smaller as the skin contact sections stand closer to the leading end 23. The skin contact sections 71Da, 71Db, 71Dc have, at the rear, respective V-grooves 71Dd, 71De, 71Df. The V-grooves 71Dd, 71De, 71Df correspond to an example of the weak section in the present invention. As illustrated in FIG. 13A and FIG. 13B, the skin contact sections 71Da, 71Db, 71Dc are configured so as to be removable, sequentially from the leading end side, through cleaving at the sites of the V-grooves 71Dd, 71De, 71Df. The size of the second pricking opening can be selected thereby in the lancet cartridge A5. The skin contact sections 71Da, 71Db, 71Dc may be configured to have dissimilar shapes in accordance with the pricking site, instead of being configured to have dissimilar sizes of the second pricking openings 71Dg, 71Dh, 71Di.

In the present embodiment, a skin contact section having a second pricking opening of appropriate size can be selected, as the case may require, from among the plurality of skin contact sections 71Da, 71Db, 71Dc. The collection amount of blood can be finely adjusted as a result. It becomes thus possible to secure a sufficient blood amount for measurement, since blood collection can be performed appropriately at a plurality of dissimilar collection sites, in cases where the shape of the leading end 23 of the lancet holder 2 is to be modifiable to a shape that conforms to the shape of the pricking site.

Figure 14:
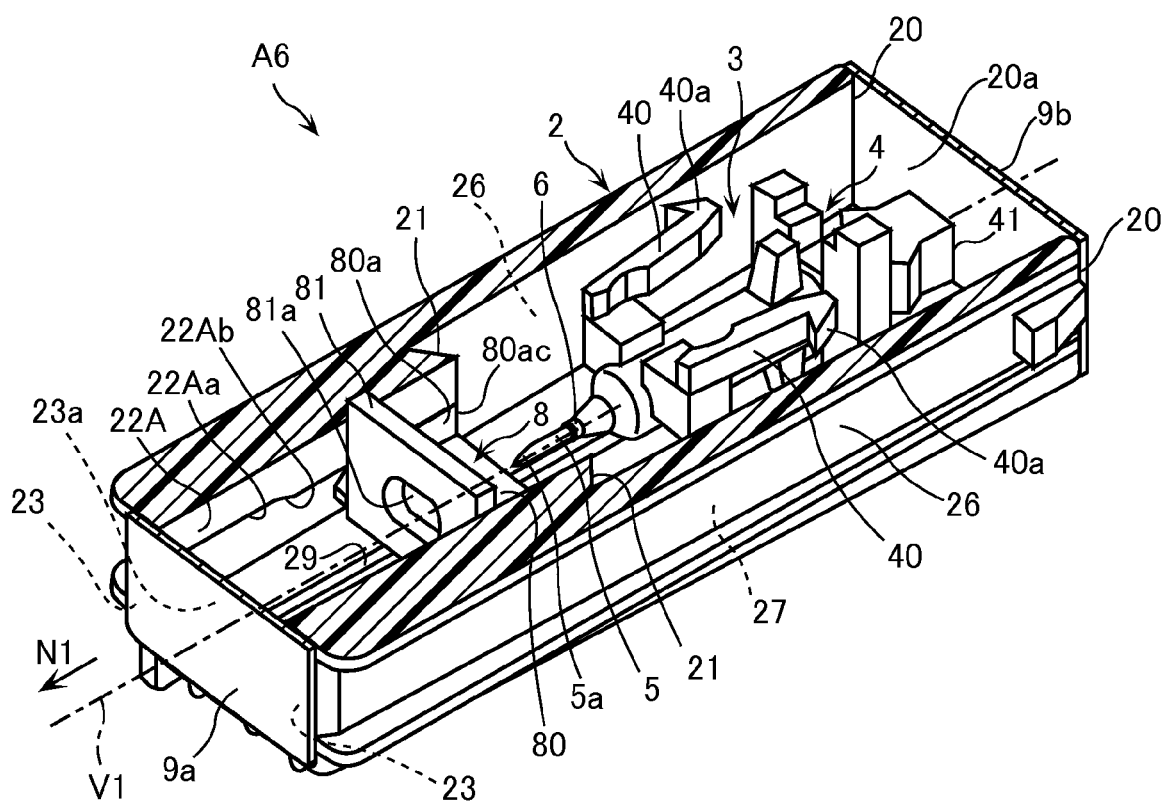
FIG. 14 is a cross-sectional perspective-view diagram illustrating another example of a lancet cartridge according to the present invention.

FIG. 14 illustrates another embodiment of a lancet cartridge according to the present invention. A lancet cartridge A6 differs from the lancet cartridge A1 explained above as regards the following features. Specifically, a movable skin contact member 8 is provided instead of the protective cap 7. The configuration of the slope sections 22A is also different herein. Further, the lancet cartridge A6 is provided with a leading end sealing material 9a and a rear end sealing material 9b. The slit 24 is omitted.

The lancet cartridge A6 has a pair of slope sections 22A on the inner faces of the left and right side wall sections 26 of the lancet holder 2. The slope sections 22A are provided contiguously to the stopper sections 21, in the pricking direction N1, and have slope faces 22Aa. When pressed from behind, the below-described movable skin contact member 8 moves along the slope faces 22Aa. The rear portions of the slope sections 22A are configured in such a manner that below-described sledge sections 80a of the movable skin contact member 8 can mate between the slope faces 22Aa and the bottom wall section 27. The sledge sections 80a are configured so as to be movable by virtue of upward-slanting steps 22Ab that are provided at portions on the pricking direction N1 side of the slope sections 22A.

The movable skin contact member 8 is a portion that comes into contact with the skin of the blood sampling subject during blood sampling. The color of the movable skin contact member 8 is different from that of lancet holder 2. For instance, the movable skin contact member 8 is colored in pink, and the lancet holder 2 is colored in light grey. With the lancet cartridge A6 not yet in use, the movable skin contact member 8 is disposed in the interior of the lancet holder 2. The lancet cartridge A6 moves in the pricking direction N1 when fitted to the pricking instrument 1. As a result, the movable skin contact member 8 becomes visible from outside. The movable skin contact member 8 is provided with a slide section 80 and a skin contact section 81.

The slide section 80 is provided for the purpose of enabling the movable skin contact member 8 to slide smoothly in the lancet holder 2. As illustrated in FIG. 14, the slide section 80 is a plate-like member that is disposed so as to be parallel to the bottom wall section 27 of the lancet holder 2. The bottom face of the slide section 80 is configured so as to slide over a rail section 29 that is provided in the inner face of the bottom wall section 27.

The protective section 80 has the pair of sledge sections 80a on both side faces. The purpose of the sledge sections 80a is to enable the movable skin contact member 8 to be appropriately held in the lancet holder 2 and to move smoothly. The sledge sections 80a have pressing sections 80ac for the purpose of enabling the pricking mechanism of the pricking instrument 1 to press the movable skin contact member 8 in the pricking direction N1. The slide section 80 and the skin contact section 81 become pressed in the pricking direction N1 when the pressing sections 80ac are pressed from behind. Before fitting to the pricking instrument 1, the sledge sections 80a mate between the bottom wall section 27 and the slope faces 22Aa of the slope sections 22A, and become fixed in the interior of the lancet holder 2. When the lancet cartridge A6 is inserted in the fitting section 10 of the pricking instrument 1, the pressing sections 80ac of the sledge sections 80a are pressed from behind, and mating between the sledge sections 80a and the slope faces 22Aa is released. As described above, the upward-slanting steps 22Ab are provided in the slope faces 22Aa of the slope sections 22A. Therefore, the movable skin contact member 8 can move freely when pressed up to that position. When the slope faces 22Aa are pressed next, the movable skin contact member 8 moves up to the position of the leading end 23 of the lancet cartridge A6. When the movable skin contact member 8 moves up to the position of the leading end 23 of the lancet cartridge A6, lower tapered sections 80ab of the sledge sections 80a engage with the protrusions 25. As a result, the movable skin contact member 8 stops at the position of the leading end 23 of the lancet cartridge A6.

The skin contact section 81 is a plate-like member erected at the leading end of the slide section 80, in a direction that intersects the pricking direction N1. More specifically, the skin contact section 81 is provided so as to be perpendicular to the pricking direction N1. The skin contact section 81 is configured so as to be accommodated in the first pricking opening 23a when the movable skin contact member 8 moves in the pricking direction N1. The second pricking opening 81a is provided at substantially the central section of the skin contact section 81. The second pricking opening 81a is configured in such a manner so as to reach a position that is crossed by the pricking track V1 when the second pricking opening 81a moves up to the position of the first pricking opening 23a. The tip 5a of the pricking member 5 moves along the pricking track V1 in the pricking direction N1, and can protrude through the second pricking opening 81a. A peripheral section of the second pricking opening 81a of the skin contact section 81 is formed to a planar shape. Needless to say, the shape of the peripheral section of the second pricking opening 81a may be any shape, so long as blood sampling can take place appropriately, and may be a curved shape that conforms to the blood sampling site, for instance, the fingertips, palms, forearms, earlobes and the like.

The purpose of the leading end sealing material 9a is to plug the first pricking opening 23a. The purpose of the rear end sealing material 9b is to plug the rear end opening 20a. No slit 24 is provided in the lancet holder 2. The leading end sealing material 9a and the rear end sealing material 9b are stripped off upon fitting of the lancet cartridge A6 to the pricking instrument 1. The tip 5a of the pricking member 5 is uncovered in the lancet cartridge A6. As a result, the tip 5a of the pricking member 5 can be kept sterile, since the interior of the lancet holder 2 is sealed off.

The operation of the lancet cartridge A6 is explained next with reference to FIG. 15A and FIG. 15B.

Figure 15A:
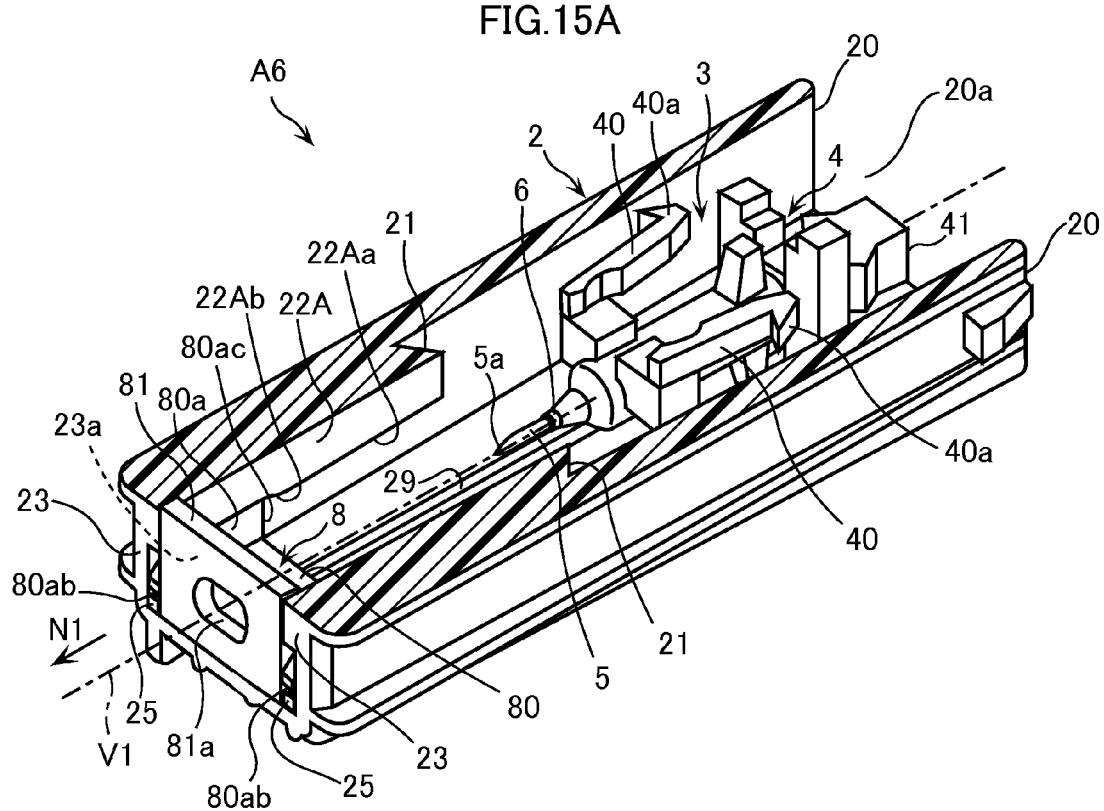
FIG. 15A and FIG. 15B are cross-sectional perspective-view diagrams for explaining the operation of the lancet cartridge illustrated in FIG. 14.
Figure 15B:
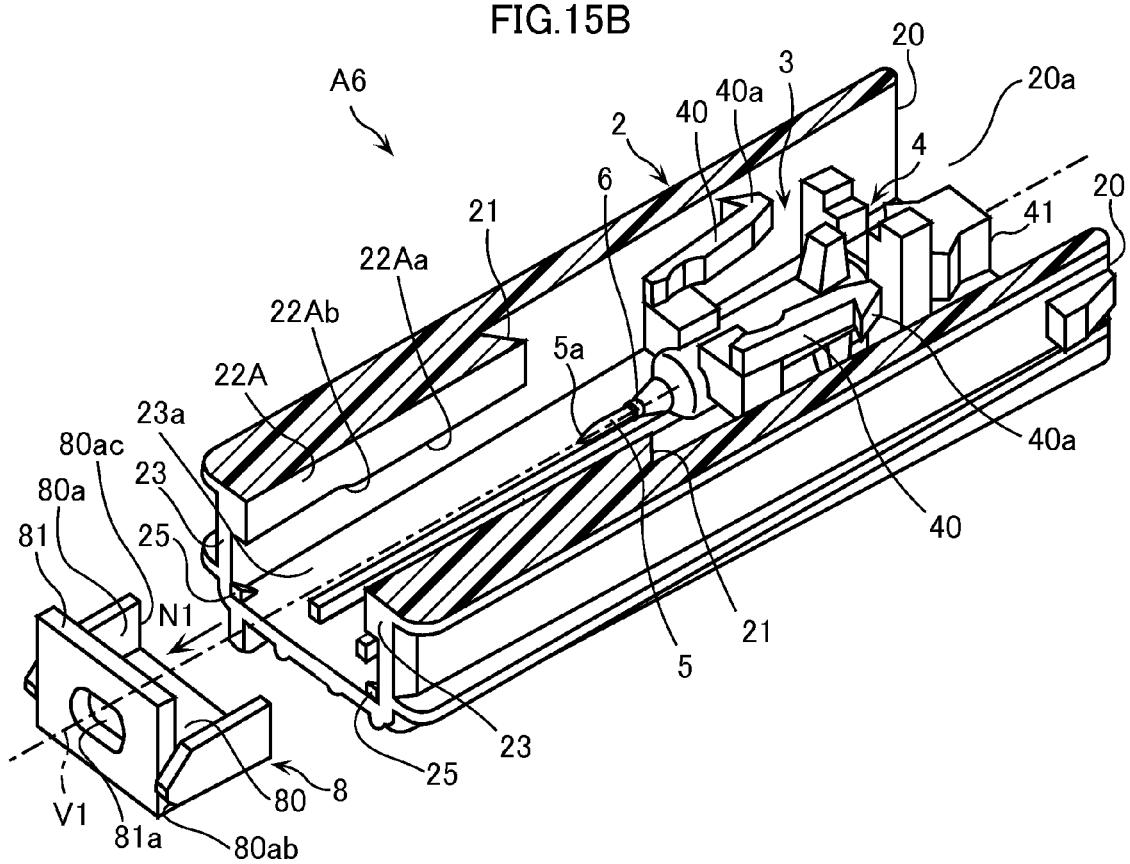

As illustrated in FIG. 15A, when the movable skin contact member 8 is pressed in the pricking direction N1, the skin contact section 81 becomes accommodated in the first pricking opening 23a, and plugs the first pricking opening 23a. At this time, the movable skin contact member 8 is prevented from coming off the lancet holder 2 through engagement of the lower tapered sections 80ab of the sledge sections 80a with the protrusions 25.

In a case where an appropriate blood sampling amount cannot be obtained in that the tip 5a of the pricking member 5 protrudes through the second pricking opening 81a, the movable skin contact member 8 is removed off the leading end 23 of the lancet holder 2 in a state where the lancet cartridge A6 is fitted to the pricking instrument 1. Specifically, as shown in FIG. 15(B), engagement of the lower tapered sections 80ab of the sledge sections 80a with the protrusions 25 is lifted, and the movable skin contact member 8 is removed off the lancet holder 2. As a result, the tip 5a of the pricking member 5 protrudes now through the first pricking opening 23a.

In the lancet cartridge A6, as in the case of the above-described lancet cartridge A2, a cleavable weak section may be formed in the movable skin contact member 8, to enable removal of the skin contact section 81. As in the case of the lancet A3, the skin contact section 81 may be made up of a plurality of plate-like members, partitioned by the weak sections, so as to surround the second pricking opening 81a, in a plan view. The size of the second pricking opening 81a can be through sequential cleaving of the plurality of plate-like members from the inward side.

As in the case of the above-described lancet cartridge A4, the skin contact section 81 may be shaped as a spiral centered on the second pricking opening 81a. In this case, the size of the second pricking opening 81a can be selected through formation of a cleavable weak section at a predetermined location in the spiral, and through sequential cleaving of the weak sections from the inward side of the spiral.

As in the case of the above-described lancet cartridge A5, the skin contact section 81 of the lancet cartridge A6 may be configured in the form of a plurality of stacked sections in the pricking direction N1. In that case, the size of the second pricking opening 81a can be selected by forming second pricking openings 81a of the skin contact section 81 to become smaller towards the leading end side, and through sequential removal of the leading end-side skin contact sections 81. The plurality of stacked skin contact sections 81 may have dissimilar shapes in accordance with the pricking site of the blood sampling subject.

During use, the skin contact section 81 of the movable skin contact member 8 in the present embodiment is disposed so as to plug the first pricking opening 23a, as described above. The skin contact section 81 is large enough to be visible from outside. Accordingly, this allows discriminating easily whether the lancet cartridge A6 has already been used or not. Re-use of a used lancet cartridge A6 can therefore be easily prevented.

When the lancet cartridge A6 is in use, firstly the skin contact section 81 moves to the leading end 23 that is pressed against the skin of the blood sampling subject. Accordingly, the likelihood of contamination while not yet in use is low. The lancet cartridge A6 is therefore advantageous in terms of securing hygiene.

In the lancet cartridge A6, the movable skin contact member 8 and the lancet holder 2 have dissimilar colors. Therefore, it is possible to easily discriminate whether the lancet cartridge is a used one or not.

In the lancet cartridge A6, the movable skin contact member 8 can be removed from the lancet holder 2. Therefore, it becomes possible to easily modify the shape of the leading end 23 of the lancet holder 2 that is pressed against the skin of the blood sampling subject. As a result, blood can be appropriately collected at a plurality of dissimilar collection sites, and a blood amount can be secured that is sufficient for measurement. The movable skin contact member 8 is configured in such a manner that, when the latter is removed, the tip 5a of the pricking member 5 protrudes through the first pricking opening 23a. For instance, the first pricking opening 23a is formed to be relatively larger than the second pricking opening 81a. Accordingly, the first pricking opening 23a enables the skin of the blood sampling subject to be thrust deeper into the lancet holder 2 than is the case in the second pricking opening 81a. As a result, the tip 5a of the pricking member 5 pricks the skin at a deeper point, and a greater amount of blood can be collected, than when using the second pricking opening 81a. Thus, a sufficient blood amount for measurement can be secured by selecting the first pricking opening 23a or the second pricking opening 81a as the case may require. Therefore, the blood sampling amount can be adjusted in cases where the pricking depth of the pricking instrument 1 cannot be successfully adjusted, even if the lancet cartridge A6 has a mechanism for adjusting the pricking depth.

The present invention is not limited to the features of the above-described embodiments. The specific configuration of the lancet cartridge according to the present invention may accommodate various design variations.

The body fluid that can be collected using the lancet cartridge according to the present invention is not limited to blood. The lancet cartridge according to the present invention can be used for collection of other body fluids, for instance interstitial fluid or the like.

What is claimed is:

1. A lancet cartridge provided with:
   a lancet that moves along a pricking track in a pricking direction and that has a pricking member having a leading end section for pricking skin, and a main body section to which a rear end section of the pricking member is fixed; and
   a lancet holder that accommodates the lancet and that has a first pricking opening at a leading end,
   the lancet cartridge further having:
   a skin contact section, held in an interior of the lancet holder, having a second pricking opening in an opened state, and the skin contact section being formed around the second pricking opening;
   wherein the first pricking opening is formed to a size such that the skin contact section is capable of being accommodated therein,
   the lancet cartridge being configured such that when the skin contact section is pressed in the pricking direction, the skin contact section is accommodated in the first pricking opening, and the leading end section of the pricking member protrudes through the second pricking opening,
   the skin contact section preliminarily has a cleavable weak section at a predetermined location,
   a part of the skin contact section is configured to be capable of being removed from the lancet holder by cleaving of the weak section, and
   a size of the second pricking opening or a shape of the skin contact section is capable of being modified in a case where the part of the skin contact section is removed.

2. The lancet cartridge according to claim 1, further comprising:
   a protective section that is connected to the skin contact section and that covers the leading end section of the pricking member; and
   a coupling section that connects the protective section and the main body section so as to cover a periphery of the pricking member,
   wherein when the protective section is pressed in the pricking direction together with the skin contact section, in a state where the main body section is fixed to the lancet holder, the coupling section breaks and the protective section separates from the main body section, and moreover the leading end section of the pricking member becomes exposed; and
   subsequently, when the protective section and the skin contact section are pressed in the pricking direction, the protective section moves off the pricking track of the pricking member, and the second pricking opening is disposed on the pricking track.

3. The lancet cartridge according to claim 2,
   wherein the skin contact section or the protective section has a lug section to be gripped upon the removal.

4. The lancet cartridge according to claim 3,
   wherein a slit is provided in the lancet holder; and
   the lug section protrudes through the slit when the skin contact section or the protective section is pressed in the pricking direction.

5. A lancet cartridge provided with:
a lancet that moves along a pricking track in a pricking direction and that has a pricking member having a leading end section for pricking skin, and a main body section to which a rear end section of the pricking member is fixed; and
a lancet holder that accommodates the lancet and that has a first pricking opening at a leading end,
the lancet cartridge further having:
a skin contact section, held in an interior of the lancet holder, and having a second pricking opening;
wherein the first pricking opening is formed to a size such that the skin contact section is capable of being accommodated therein,
the lancet cartridge being configured such that when the skin contact section is pressed in the pricking direction, the skin contact section is accommodated in the first pricking opening, and the leading end section of the pricking member protrudes through the second pricking opening,
a part or all of the skin contact section is capable of being removed from the lancet holder, and
a size of the second pricking opening or a shape of the skin contact section is capable of being modified in a case where the part of the skin contact section is removed, or
the leading end section of the pricking member protrudes through the first pricking opening in a case where all of the skin contact section is removed,
wherein the skin contact section has a cleavable weak section, such that the skin contact section is capable of being removed by cleaving of the weak section,
wherein the skin contact section is a laminated body of a plurality of skin contact sections stacked in the pricking direction; and the second pricking opening is formed so as to become smaller as the skin contact sections are disposed closer to the leading end, such that the size of the second pricking opening is capable of being selected by sequentially cleaving the skin contact sections from the skin contact section on the leading end.

6. A lancet cartridge provided with:
a lancet that moves along a pricking track in a pricking direction and that has a pricking member having a leading end section for pricking skin, and a main body section to which a rear end section of the pricking member is fixed; and
a lancet holder that accommodates the lancet and that has a first pricking opening at a leading end,
the lancet cartridge further having:
a skin contact section, held in an interior of the lancet holder, and having a second pricking opening;
wherein the first pricking opening is formed to a size such that the skin contact section is capable of being accommodated therein,
the lancet cartridge being configured such that when the skin contact section is pressed in the pricking direction, the skin contact section is accommodated in the first pricking opening, and the leading end section of the pricking member protrudes through the second pricking opening,
a part or all of the skin contact section is capable of being removed from the lancet holder, and
a size of the second pricking opening or a shape of the skin contact section is capable of being modified in a case where the part of the skin contact section is removed, or
the leading end section of the pricking member protrudes through the first pricking opening in a case where all of the skin contact section is removed,
wherein the skin contact section has a cleavable weak section, such that the skin contact section is capable of being removed by cleaving of the weak section,
wherein the skin contact section is a laminated body of a plurality of skin contact sections stacked in the pricking direction, the skin contact sections having dissimilar shapes according to pricking sites.

7. A lancet cartridge provided with:
a lancet that moves along a pricking track in a pricking direction and that has a pricking member having a leading end section for pricking skin, and a main body section to which a rear end section of the pricking member is fixed; and
a lancet holder that accommodates the lancet and that has a first pricking opening at a leading end,
the lancet cartridge further having:
a skin contact section, held in an interior of the lancet holder, and having a second pricking opening;
wherein the first pricking opening is formed to a size such that the skin contact section is capable of being accommodated therein,
the lancet cartridge being configured such that when the skin contact section is pressed in the pricking direction, the skin contact section is accommodated in the first pricking opening, and the leading end section of the pricking member protrudes through the second pricking opening,
a part or all of the skin contact section is capable of being removed from the lancet holder, and
a size of the second pricking opening or a shape of the skin contact section is capable of being modified in a case where the part of the skin contact section is removed, or
the leading end section of the pricking member protrudes through the first pricking opening in a case where all of the skin contact section is removed,
wherein the skin contact section has a cleavable weak section, such that the skin contact section is capable of being removed by cleaving of the weak section,
wherein the skin contact section is formed of a plurality of plate-like members plurally partitioned by the weak section so as to surround the second pricking opening, in a plan view, such that the size of the second pricking opening is capable of being selected through sequentially cleaving the plurality of plate-like members from a plate-like member on an inward side.

8. A lancet cartridge provided with:
a lancet that moves along a pricking track in a pricking direction and that has a pricking member having a leading end section for pricking skin, and a main body section to which a rear end section of the pricking member is fixed; and
a lancet holder that accommodates the lancet and that has a first pricking opening at a leading end,
the lancet cartridge further having:
a skin contact section, held in an interior of the lancet holder, and having a second pricking opening;
wherein the first pricking opening is formed to a size such that the skin contact section is capable of being accommodated therein,
the lancet cartridge being configured such that when the skin contact section is pressed in the pricking direction, the skin contact section is accommodated in the first pricking opening, and the leading end section of the pricking member protrudes through the second pricking opening,
a part or all of the skin contact section is capable of being removed from the lancet holder, and a size of the second pricking opening or a shape of the skin contact section is capable of being modified in a case where the part of the skin contact section is removed, or the leading end section of the pricking member protrudes through the first pricking opening in a case where all of the skin contact section is removed, wherein the skin contact section has a cleavable weak section, such that the skin contact section is capable of being removed by cleaving of the weak section, wherein the skin contact section is shaped as a spiral centered on the second pricking opening, and the weak section is formed at a predetermined location of the spiral, such that the size of the second pricking opening is capable of being selected by sequentially cleaving weak sections on the weak section on an inward side.

9. A lancet cartridge provided with:

a lancet that moves along a pricking track in a pricking direction and that has a pricking member having a leading end section for pricking skin, and a main body section to which a rear end section of the pricking member is fixed; and a lancet holder that accommodates the lancet and that has a first pricking opening at a leading end, the lancet cartridge further having:

a skin contact section, held in an interior of the lancet holder, and having a second pricking opening, the second pricking opening being off the pricking track;

a protective section that is connected to the skin contact section and that covers the leading end section of the pricking member; and a slope section, provided in the interior of the lancet holder, and facing in the pricking direction, wherein the skin contact section moves along the slope section in the pricking direction, the first pricking opening is formed to a size such that the skin contact section is capable of being accommodated therein, the lancet cartridge being configured such that when the protective section and the skin contact section are pressed in the pricking direction along the slope section, the protective section separates from the leading end section and moves off the pricking track of the pricking member, the skin contact section is accommodated in the first pricking opening, the second pricking opening is disposed on the pricking track, and the leading end section of the pricking member protrudes through the second pricking opening.

10. The lancet cartridge according to claim 9, further comprising:

a coupling section that connects the protective section and the main body section so as to cover a periphery of the pricking member, wherein when the protective section is pressed in the pricking direction together with the skin contact section, in a state where the main body section is fixed to the lancet holder, the coupling section breaks and the protective section separates from the main body section, and moreover the leading end section of the pricking member becomes exposed.

11. A lancet cartridge provided with:

a lancet that moves along a pricking track in a pricking direction and that has a pricking member having a leading end section for pricking skin, and a main body section to which a rear end section of the pricking member is fixed; and a lancet holder that accommodates the lancet and that has a first pricking opening at a leading end, the lancet cartridge further having:

a skin contact section, held in an interior of the lancet holder, having a second pricking opening in an opened state, and the skin contact section being formed around the second pricking opening;

wherein the first pricking opening is formed to a size such that the skin contact section is capable of being accommodated therein, the lancet cartridge being configured such that when the skin contact section is pressed in the pricking direction from the interior to the leading end, the skin contact section is accommodated in the first pricking opening, and the leading end section of the pricking member protrudes through the second pricking opening, all of the skin contact section is configured to be capable of being removed from the lancet holder in a state that the lancet is held in the lancet holder, and the leading end section of the pricking member protrudes through the first pricking opening in a case where all of the skin contact section is removed.

12. The lancet cartridge according to claim 11, further comprising:

a protective section that is connected to the skin contact section and that covers the leading end section of the pricking member; and a coupling section that connects the protective section and the main body section so as to cover a periphery of the pricking member, wherein when the protective section is pressed in the pricking direction together with the skin contact section, in a state where the main body section is fixed to the lancet holder, the coupling section breaks and the protective section separates from the main body section, and moreover the leading end section of the pricking member becomes exposed; and subsequently, when the protective section and the skin contact section are pressed in the pricking direction, the protective section moves off the pricking track of the pricking member, and the second pricking opening is disposed on the pricking track.

13. The lancet cartridge according to claim 12, wherein the skin contact section or the protective section has a lug section to be gripped upon the removal.

14. The lancet cartridge according to claim 13, wherein a slit is provided in the lancet holder; and the lug section protrudes through the slit when the skin contact section or the protective section is pressed in the pricking direction.

15. The lancet cartridge according to claim 11, wherein the skin contact section preliminarily has a cleavable weak section at a predetermined location, such that a part of the skin contact section is capable of being removed by cleaving of the weak section.

* * * * *